(12) United States Patent
Blauer

(10) Patent No.: US 10,820,673 B1
(45) Date of Patent: Nov. 3, 2020

(54) CARRY BAG

(71) Applicant: Blauer Manufacturing Company, Inc., Boston, MA (US)

(72) Inventor: Stephen J Blauer, Lexington, MA (US)

(73) Assignee: Blauer Manufacturing Company, Inc., Boston, MA (US)

( * ) Notice: Subject to any disclaimer, the term of this patent is extended or adjusted under 35 U.S.C. 154(b) by 0 days.

(21) Appl. No.: 16/511,435

(22) Filed: Jul. 15, 2019

Related U.S. Application Data

(60) Provisional application No. 62/698,444, filed on Jul. 16, 2018.

(51) Int. Cl.
| | |
|---|---|
| *A45C 13/02* | (2006.01) |
| *A45F 3/04* | (2006.01) |
| *A45C 5/03* | (2006.01) |
| *A45C 11/00* | (2006.01) |
| *A61F 17/00* | (2006.01) |

(52) U.S. Cl.
CPC ............... *A45C 5/03* (2013.01); *A45C 13/02* (2013.01); *A45F 3/04* (2013.01); *A45C 2011/007* (2013.01); *A45F 2003/045* (2013.01); *A61F 17/00* (2013.01)

(58) Field of Classification Search
CPC .............. A45C 13/02; A45C 2005/037; A45C 2011/007; A45C 13/08; A45F 3/02; A61B 2050/0056; B65D 23/102; Y10S 206/811
See application file for complete search history.

(56) References Cited

U.S. PATENT DOCUMENTS

| | | | |
|---|---|---|---|
| 1,644,830 A | 10/1927 | Henderson | |
| 2,648,366 A | 8/1953 | Lona et al. | |
| 3,504,787 A | 4/1970 | Brockway | |
| 4,169,550 A | 10/1979 | Williams | |
| 4,241,833 A | 12/1980 | Luebcke | |
| 4,513,866 A | 4/1985 | Thomas | |
| 5,207,303 A | 5/1993 | Oswalt et al. | |
| 5,292,000 A * | 3/1994 | Levy ................. | A61B 10/0096 206/456 |
| 5,653,318 A | 8/1997 | Field | |
| 5,848,700 A | 12/1998 | Horn | |
| 5,897,209 A | 4/1999 | Roegner | |
| 6,116,045 A * | 9/2000 | Hodosh ................. | A45C 11/20 62/457.4 |

(Continued)

*Primary Examiner* — Brian D Nash
(74) *Attorney, Agent, or Firm* — Altman & Martin; Steven K Martin

(57) ABSTRACT

A completely bleach-cleanable, clamshell bag composed of molded emulsified EVA. A base and lid form a generally rectangular compartment that removably holds a variety of caddies via PALS strips. A lid lip engages with a base lip to form a liquid-resistant seal. The hinges are flexible, coated webbing straps for durability and to facilitate cleaning. The latch includes side release buckles on flexible, coated webbing straps. Handles are composed of flexible, coated webbing straps. A recess in the base floor holds an oxygen cylinder with an attached regulator, retained by an elastic cylinder harness designed for cylinders of different lengths. The bag includes a waist belt, a pair of shoulder straps, and a carry strap, all of which are removable to facilitate cleaning. An optional flashlight arm can rotate and pivot removably attaches a flashlight.

19 Claims, 20 Drawing Sheets

(56) References Cited

U.S. PATENT DOCUMENTS

| | | | | |
|---|---|---|---|---|
| 6,164,450 A | * | 12/2000 | Benedetti | A61H 35/02 |
| | | | | 206/570 |
| 6,454,097 B1 | | 9/2002 | Blanco | |
| 6,866,151 B2 | | 3/2005 | Mousset et al. | |
| 7,048,114 B1 | * | 5/2006 | Prottas | A45C 5/005 |
| | | | | 132/287 |
| 7,086,397 B2 | * | 8/2006 | Spruiell | A61M 16/10 |
| | | | | 128/200.24 |
| 7,775,365 B1 | * | 8/2010 | More | A61F 2/76 |
| | | | | 206/572 |
| 9,072,653 B2 | * | 7/2015 | Nemard | A61B 50/31 |
| 2002/0043534 A1 | * | 4/2002 | Uke | E05B 65/5276 |
| | | | | 220/4.21 |
| 2006/0289329 A1 | | 12/2006 | Miller | |
| 2010/0059560 A1 | | 3/2010 | Lanum | |
| 2010/0096286 A1 | | 4/2010 | Ma et al. | |
| 2010/0307649 A1 | | 12/2010 | Dominguez | |
| 2012/0145151 A1 | * | 6/2012 | Bergman | A61M 16/0078 |
| | | | | 128/204.21 |

* cited by examiner

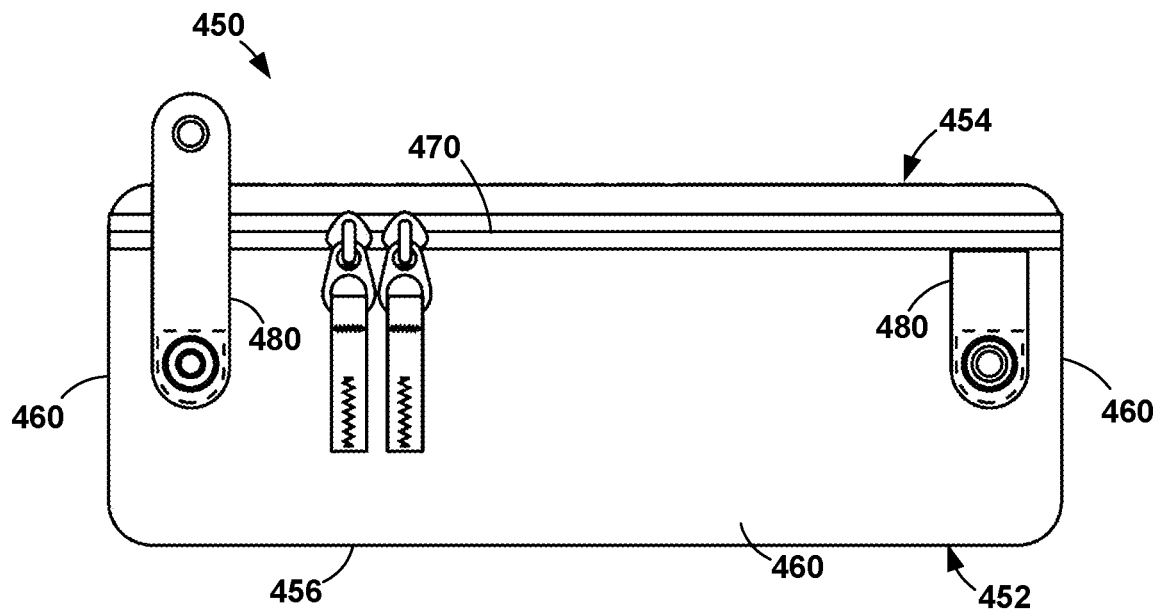
FIG. 32
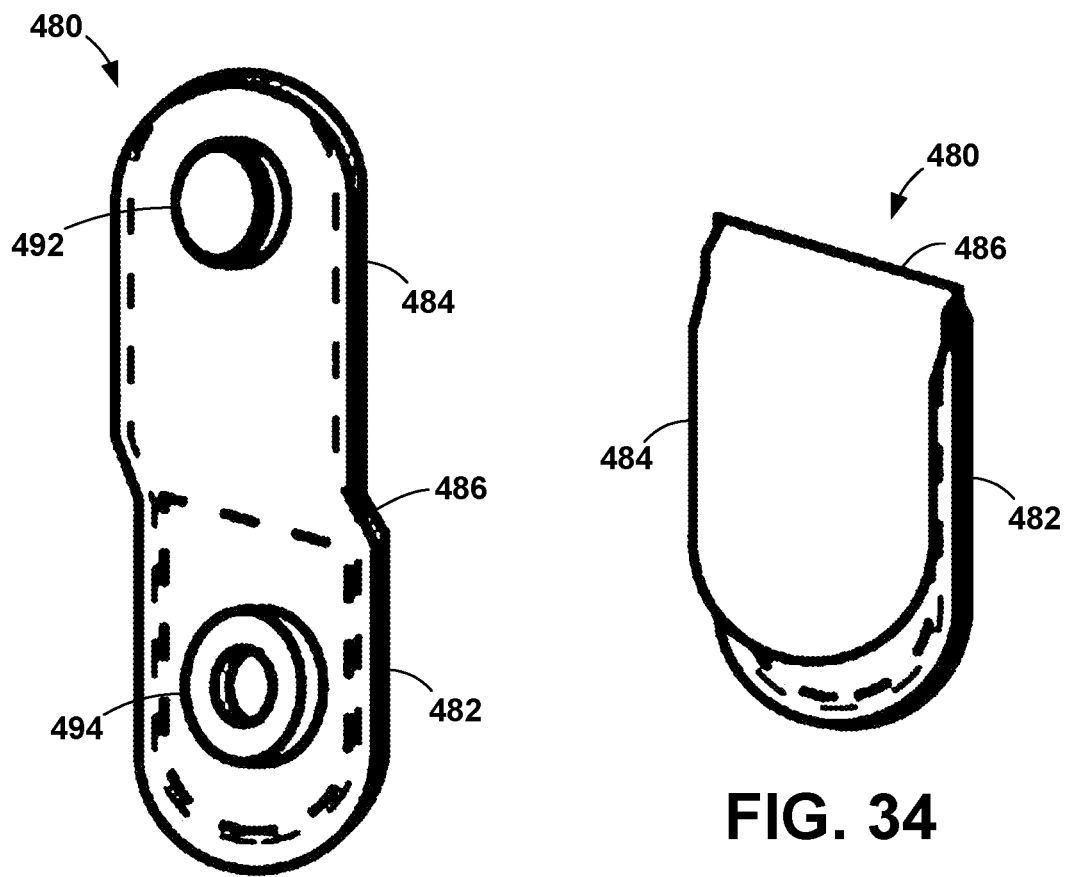
FIG. 33
FIG. 34

CARRY BAG

STATEMENT REGARDING FEDERALLY SPONSORED RESEARCH OR DEVELOPMENT

Not Applicable

REFERENCE TO A SEQUENCE LISTING, A TABLE, OR A COMPUTER PROGRAM LISTING COMPACT DISK APPENDIX

Not Applicable

BACKGROUND OF THE INVENTION

1. Field of the Invention

The present invention relates to bags for emergency medical supplies.

2. Description of the Related Art

Emergency medical bags are currently made from large denier (500-1500) woven fabrics, mostly nylons and polyesters. They are often treated with durable water repellant chemicals (DWR) to resist water uptake. Some use polyurethane (PU) or acrylic coatings on the inside of the materials for water resistance and durability, and some may use limited outer coatings, for example on the bottom of the bag, which might come in contact with surface water. Trims used on the bags such as straps, zippers and hook and loop closures are ordinary commercial grade trims as might be used on luggage. Threads used to sew the seams of the bags together are polyester or nylon core polyester or nylon wrapped.

While the materials work well to hold the contents in the bags, are durable, and affordable, the fabrics, trims, and thread/seams also tend to absorb blood, other body fluids, and microbiology in the vicinity of the patients being treated. EMTs then carry these bags to the next call and bring potential pathogens with them. Even fabrics treated with DWR lose their ability to repel fluids and water as soon as surface dirt penetrates their fibers. Some bags can potentially be washed but washing them with bleach or other chemicals, which might kill microbiology, can also ruin the bags.

BRIEF SUMMARY OF THE INVENTION

The present invention is a totally bleach-cleanable bag. The clamshell design forms a liquid-resistant seal. The bag is composed of molded emulsified (foam) ethylene-vinyl acetate copolymer (EVA). All surfaces are cleanable with bleach or hospital-grade wipes.

Another feature is the oxygen cylinder recess with an elasticized harness so that a cylinder can be added and removed without adjustment.

The bag has a shell with a base and a lid that form a generally rectangular compartment within. They are composed of an impermeable material that is somewhat flexible. A preferred material is an emulsified (foam) ethylene-vinyl acetate copolymer (EVA). Optionally, the outer surfaces are covered with a skin or laminate to provide color and texture, abrasion resistance, cleaning facilitation, and a bit of tear strength. In one configuration, the skin is a polyurethane (PU), thermoplastic polyurethane (TPU), or polyvinyl chloride (PVC) laminate.

The entire circumferential edges of the base and lid are formed into lips. When the bag is closed, the lid lip engages with the base lip to form a seal that is resistant to liquid passing through.

Mounting brackets are permanently attached to various locations on the base and lid, and are designed for several uses. Each mounting bracket is a flat, metallic piece, preferably stamped aluminum that is powder-coated or anodized. The mounting bracket is generally triangular. Strap slots extend along a short side and a long side. Each mounting bracket is permanently attached by brass or stainless-steel rivets. Preferably, the manner of mounting makes the attachment resistant to liquid passing through.

The base and lid are attached together by two or more hinges that are each a flexible strap composed of a polyester or nylon webbing that is coated with PU, TPU, or PVC for durability and to facilitate cleaning. One strap end is permanently attached to the base at a hinge base mounting bracket and the other end is permanently attached to the lid at a hinge lid mounting bracket.

A latching mechanism preferably employs two or more side-release buckles. The female components are permanently attached to the lid by rivets. The male components are attached to the free end of straps. The other end of each strap is permanently attached to the base at latch base mounting brackets. Optionally, the length of each strap is adjustable by looping the strap through a square ring on the male component, as is well-known in the art. The straps are composed of a polyester or nylon webbing that is coated with a PU, TPU, or PVC for durability and to facilitate cleaning.

The bag has a hinge side handle and a latch side handle. Each is composed of a base strap and loop strap, each of which is composed of a polyester or nylon webbing coated with a PU, TPU, or PVC for durability and to facilitate cleaning. The loop strap is laterally stitched to the base strap to form an elongated, longitudinal handle loop and lateral carabiner loops straddling the handle loop. The ends of the handles are permanently attached mounting brackets.

The base floor optionally has a recess for holding an oxygen cylinder with an attached regulator. The cylinder is retained in the recess by an elastic cylinder harness that is designed for cylinders of different lengths. An optional foam pad protects the wearer's back from the cylinder.

The bag includes a waist belt, a pair of shoulder straps, and a carry strap. All of these components are detachably attached to the base so that they can be removed to facilitate cleaning. Optionally, the bag comes with multiple sets of these components so they can be swapped out after each job to await cleaning. Optionally, these components are disposable.

Optionally, the bag includes a flashlight arm to which a flashlight can be removably attached via a cylindrical bracket at the end of the arm. The arm attaches inside the base so it can rotate and pivot.

The lid optionally includes a removable divider that separates the lid into two compartments. The lid and base optionally include compression straps.

Strips of Pouch Attachment Ladder System (PALS) webbing are attached to the inside surface of the base and lid and on both sides of the divider. The present invention includes caddies of various sizes that are removably affixed to the inside of the bag via the PALS strips.

Objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein:

FIG. 32 is a side view of a closed caddy;

FIG. 33 is a detailed perspective view of an open caddy latch;

FIG. 34 is a detailed perspective view of a closed caddy latch; and

DETAILED DESCRIPTION OF THE INVENTION

Figure 1:
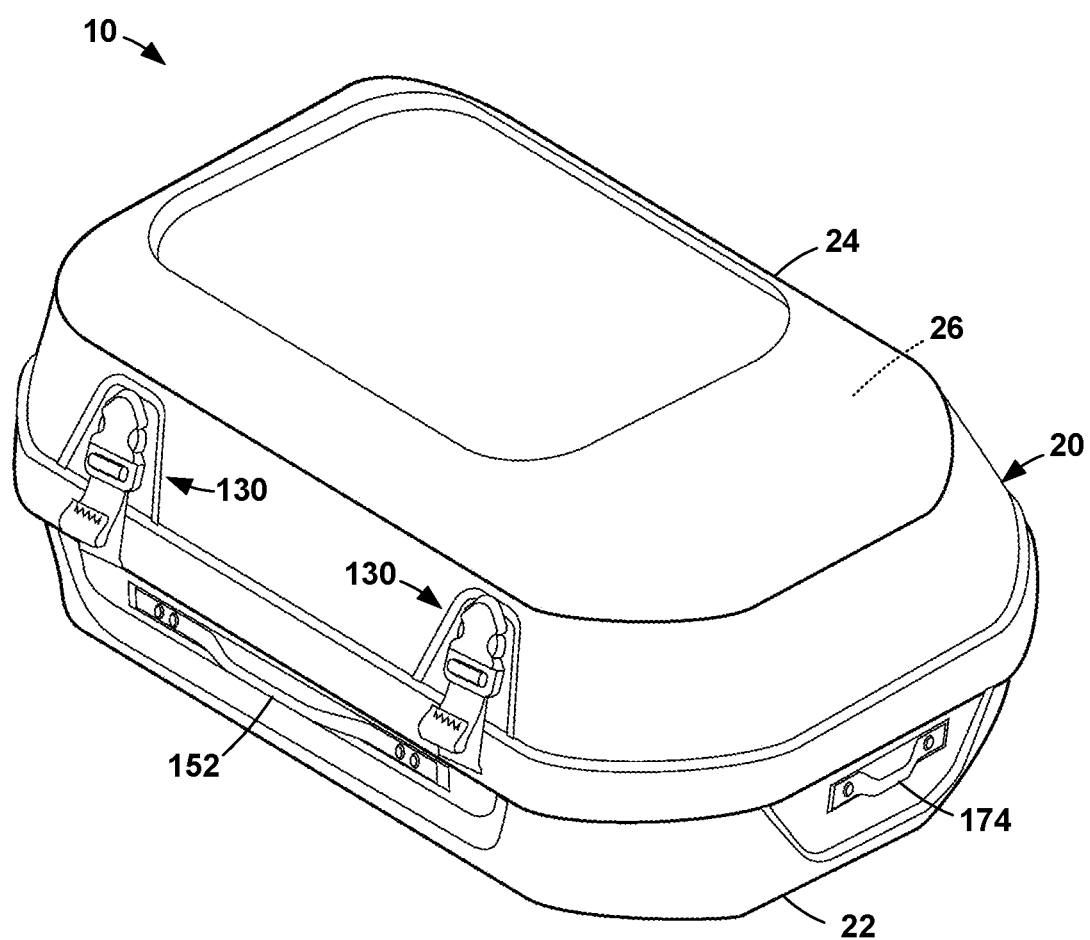
FIG. 1 is a perspective view of the bag of the present invention in the closed position.

The present application hereby incorporates by reference in its entirety U.S. Provisional Patent Application No. 62/698,444, on which this application is based.

The bag of the present invention is a totally bleach-cleanable bag for EMTs and paramedics so that biological pathogens can be removed from the bag on a regular basis. The bag is unique in that all of the materials used are 100% cleanable, either coated (with the exception of the removable shoulder straps and the interior caddies) or laminated, or made from a waterproof and cleanable materials. The bag has a clamshell design wherein the lid closes over the base to form a liquid-resistant seal. The outer material is molded EVA with a patterned skin. All surfaces are cleanable with bleach or hospital-grade wipes.

Another unique feature is the oxygen cylinder recess and harness. The harness is elasticized so that a cylinder can be added and removed without adjustment.

As shown in FIGS. 1-8, the bag 10 of the present invention has a shell 20 with a base 22 and a lid 24 that form a compartment 26 within. The base 22 has a generally rectangular floor 30 with a long hinge side 32, a latch side 34 opposite the hinge side 32, a short foot end 36 between the hinge side 32 and the latch side 34, and a short handle end 38 between the hinge side 32 and the latch side 34 and opposite the foot end 36. All of the sides 32, 34 and ends 36, 38 extend upwardly from the floor 30 at approximately 90° to form a base compartment 46. Optionally, the junctions 40 where the sides 32, 34 and ends 36, 38 extend from the floor 30 are rounded, as in FIG. 4. Optionally, the junctions 42, 44 where the sides 32, 34 and ends 36, 38 attach together are rounded, as in FIG. 7. Optionally, the rounded junctions 44 at the handle end 38 are larger than the rounded junctions 42 at the foot end 36, resulting in the handle end 38 being shorter than the foot end 36, as in FIG. 7.

The lid 24 has a generally flat, rectangular roof 64 with a long hinge side 66, a latch side 68 opposed to the hinge side 66, a short foot end 70 between the hinge side 66 and the latch side 68, and a short handle end 72 between the hinge side 66 and the latch side 68 and opposed to the foot end 70. All of the sides 66, 68 and ends 70, 72 extend downwardly from the roof 64 at approximately 90° to form a lid compartment 80. Optionally, the junctions 74 where the sides 66, 68 and ends 70, 72 extend from the roof 64 are rounded or beveled, as in FIG. 4. Optionally, the junctions 76, 78 where the sides 66, 68 and ends 70, 72 attach together are beveled or rounded, as in FIG. 6. Optionally, the rounded junctions 78 at the handle end 72 are larger than the rounded junctions 76 at the foot end 70, resulting in the handle end 72 being shorter than the foot end 70, as in FIG. 6.

The present specification describes the bag 10 in three different orientations. The work orientation is when the floor 30 is horizontal such as when the bag 10 is laying on the ground or a table, as in FIGS. 2-5. The upright-carry orientation is when the foot end 36 and handle end 38 are horizontal, as in FIGS. 6 and 7. The side-carry orientation is when the hinge side 32 and latch side 34 are horizontal, as in FIG. 8.

The base 22 and lid 24 are composed of an impermeable material that is somewhat flexible. A preferred material is an emulsified (foam) ethylene-vinyl acetate copolymer (EVA). The advantage to using a flexible material, rather than a rigid material, is that the bag 10 rests against a wearer's back and is more comfortable when it can flex.

Optionally, the outer surface of the base 22 and lid 24 are covered with a skin or laminate to provide color and texture, abrasion resistance, cleaning facilitation, and a bit of tear strength. In one configuration, the skin is a polyurethane (PU), thermoplastic polyurethane (TPU), or polyvinyl chloride (PVC) laminate.

The dimensions of the bag 10 can be designed for each particular application, such as Basic Life Support and Advanced Life Support, to carry medicines exclusively, or other medical equipment used on the scene. As currently designed, the bag 10 is 60 cm from the lid foot end 70 to the lid handle end 72, 38 cm from the lid hinge side 66 to the lid latch side 68, and 26 cm from the base floor 30 to the lid roof 64.

Figure 9:
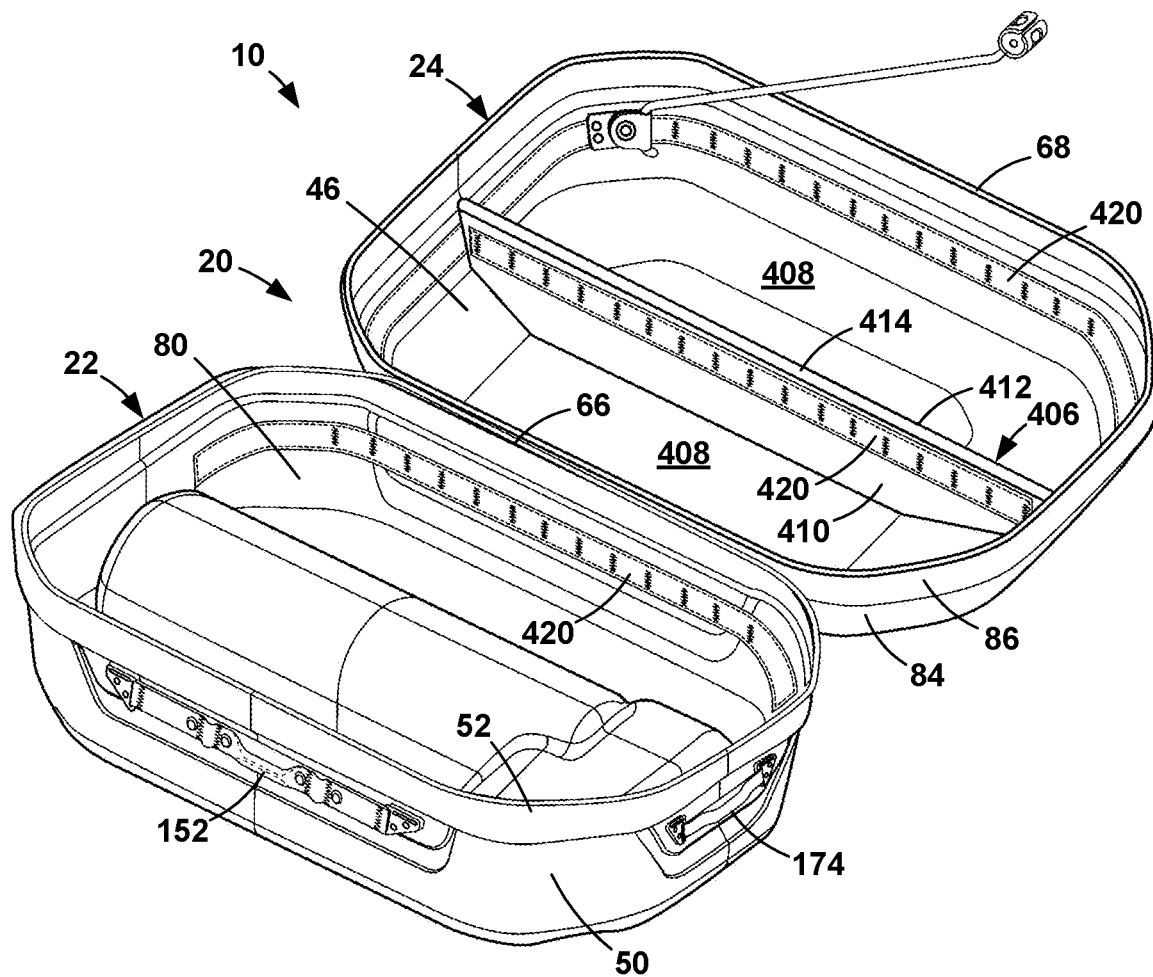
FIG. 9 is a perspective view of the bag in the opened position.
Figure 10:
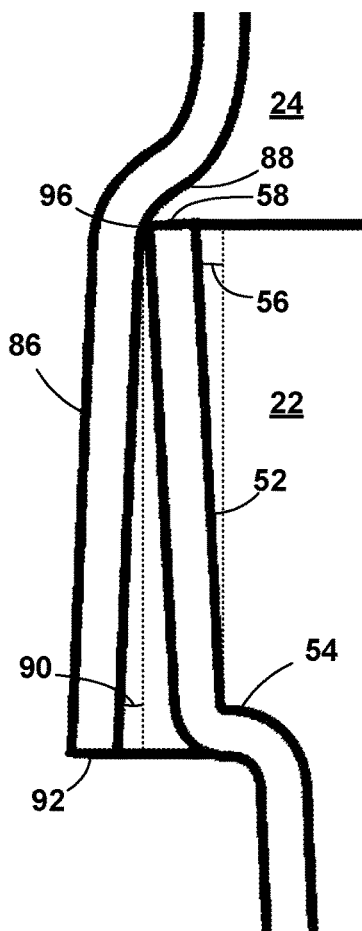
FIG. 10 is a cross-sectional, detailed view of the seal between the base and the lid.

As shown in FIG. 9, the entire circumferential edge of the base 22 is formed into a lip 52 and the entire circumferential edge of the lid 24 is formed into a lip 86. When the bag 10 is closed, the lid lip 88 engages with the base lip 52 to form a seal 96 that is resistant to liquid passing through. As shown in FIG. 10, the base lip 52 is delimited by a shoulder 54 that offsets the lip 52 outwardly and the lid lip 86 is delimited by a shoulder 88 that offsets the lid lip 86 outwardly farther than that of the base lip 52. The base lip 52 flares slightly outwardly from the shoulder 54 to the lip edge 58, as at 56 and the lid lip 86 flares outwardly from the shoulder 88 to the lip edge 92 farther than the base lip 52, as at 90. As shown in FIG. 10, when the bag 10 is closed, the lid lip 86 overlaps the base lip 52 such that the base lip 52 abuts the lid shoulder 88. When the bag 10 is secured closed, the base lip 52 and lid shoulder 88 deform slightly due to its flexibility, thereby forming the liquid-resistant seal 96 between the base 22 and lid 24.

Figure 11:
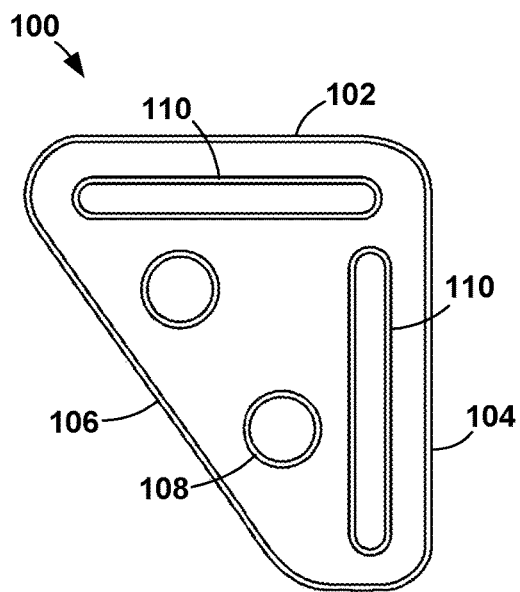
FIG. 11 is a detail view of a mounting bracket.

Mounting brackets 100a-1 (collectively, 100), shown in FIG. 11, are permanently attached to various locations on the base 22 and lid 24, and are designed for several uses. Each mounting bracket 100 is a flat, metallic piece. Preferably, the mounting bracket 100 is stamped aluminum that is powder-coated or anodized for durability. The mounting bracket 100 is generally triangular with a short side 102 and a long side 104 at a right angle to each other, and a hypotenuse 106. There are mounting holes 108 along the hypotenuse 106. Strap slots 110 extend along the short side 102 and long side 104.

The mounting bracket 100 is permanently attached to the base 22 or lid 24 by brass or stainless-steel rivets or other appropriate fasteners through the mounting holes 108. Preferably, the manner of mounting makes the attachment resistant to liquid passing through.

Figure 2:
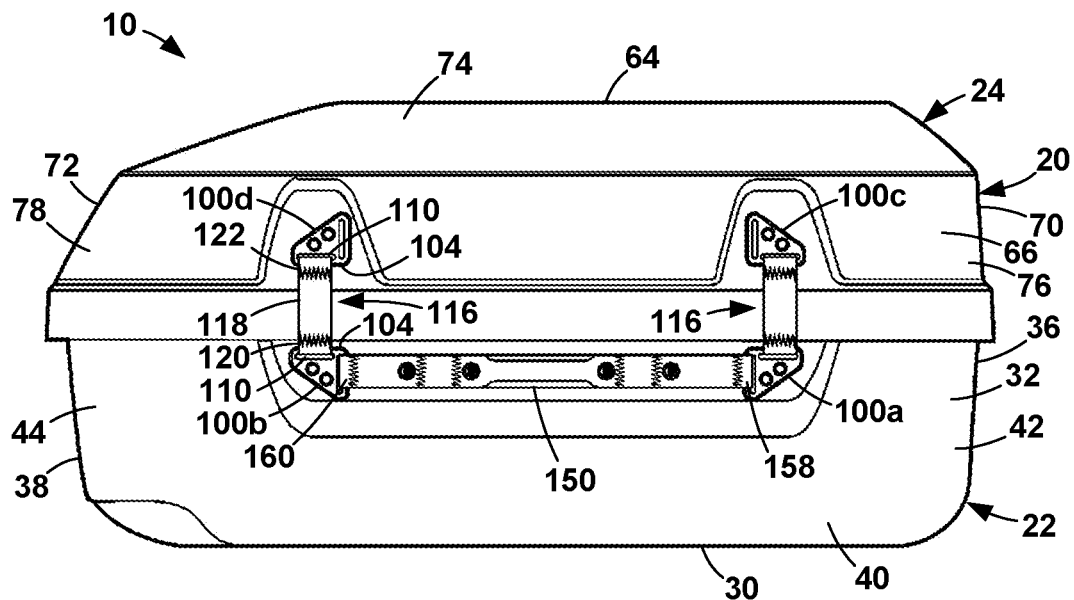
FIG. 2 is an elevational view of the hinge side of the bag in the work orientation.

The hinge side 32 of the base 22 and the hinge side 66 of the lid 24 are attached together by two or more hinges 116, as shown in FIG. 2. Each hinge 116 is a flexible strap 118 with two ends 120, 122. The straps 118 are composed of a polyester or nylon webbing that is coated with PU, TPU, or PVC for durability and to facilitate cleaning. One strap end 120 is permanently attached to the base 24 at a hinge base mounting bracket 100a, 100b. The other end 122 is permanently attached to the lid 22 at a hinge lid mounting bracket 100c, 100d. The ends 120, 122 of the straps 118 are fed through the strap slot 110 on the long side 104 of the mounting bracket 100a-d, folded over, and stitched to retain the strap 118.

Figure 3:
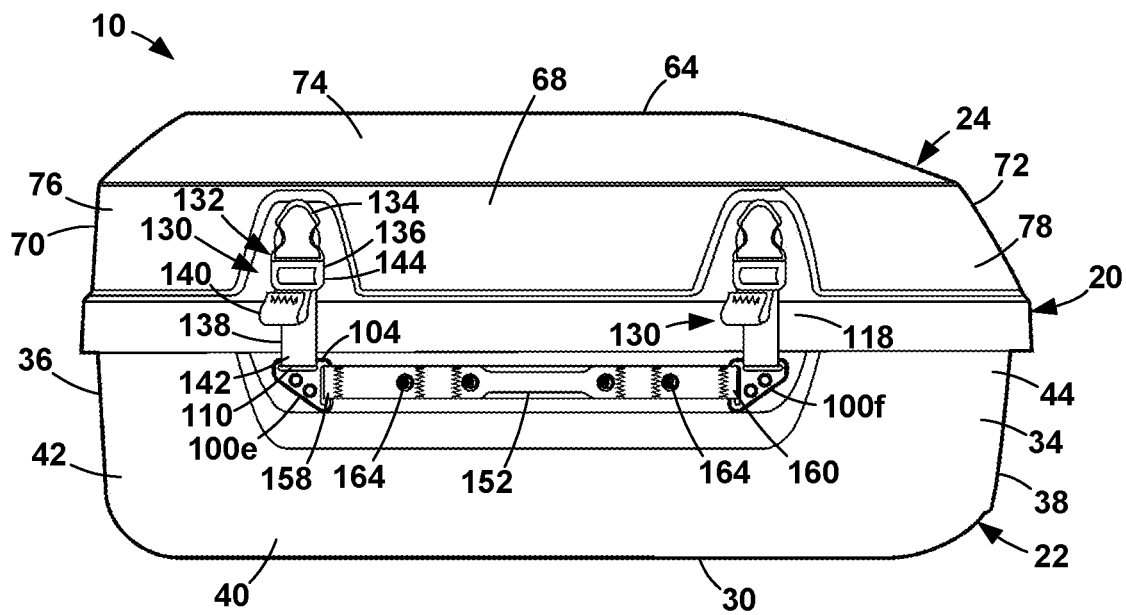
FIG. 3 is an elevational view of the latch side of the bag in the work orientation.
Figure 4:
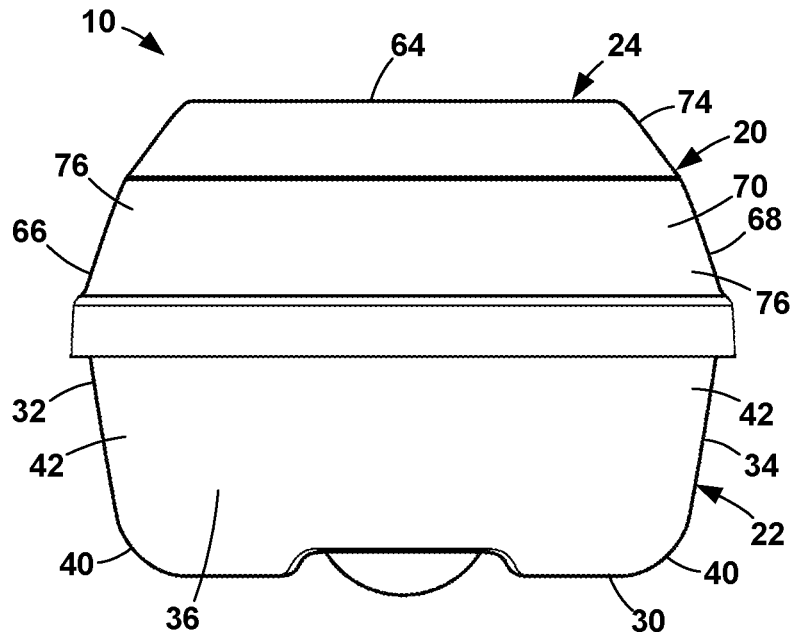
FIG. 4 is an elevational view of the foot end of the bag in the work orientation.

A latching mechanism 130 engages to secure the bag 10 closed. The preferred latching mechanism 130 employs two or more side-release buckles 132, as shown in FIG. 3. The components 134, 136 of the buckle are preferably composed of a plastic, such as an acetal resin, an example being DELRIN®. The female components 134 are permanently attached to the lid 24 by rivets. Preferably, the manner of mounting makes the attachment resistant to liquid passing through. The male components 136 are attached to the free end 140 of straps 138. The other end 142 of the straps 138 are permanently attached to the base 24 at latch base mounting brackets 100e, 100f. The ends 142 of the straps 138 are fed through a strap slot 110 on the long side 104 of the mounting bracket 100e, 100f, folded over, and stitched to retain the strap 138. The present invention contemplates that the female component 134 can be attached to the base 22 and the male component 136 can be on a strap 138 attached to the lid 24. Optionally, the length of each strap 138 is adjustable by looping the strap 138 through a square ring 144 on the male component 136, as is well-known in the art. The straps 138 are composed of a polyester or nylon webbing that is coated with a PU, TPU, or PVC for durability and to facilitate cleaning.

Figure 12:
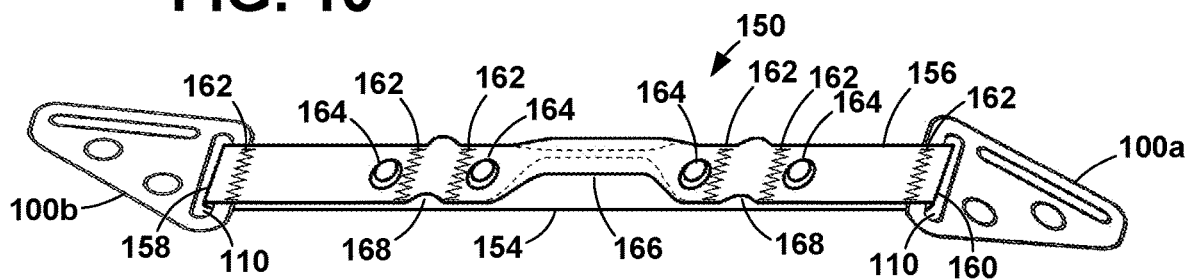
FIG. 12 is a detail view of the hinge side handle.

The bag 10 has several handles. The hinge side handle 150, shown in FIGS. 2 and 12, and the latch side handle 152, shown in FIG. 3, are identical. Each is composed of a base strap 154 and loop strap 156, each of which is composed of a polyester or nylon webbing coated with a PU, TPU, or PVC for durability and to facilitate cleaning. The loop strap 156 is laterally stitched to the base strap 154, as at 162, in such a way as to form an elongated, longitudinal handle loop 166 and lateral carabiner loops 168 straddling the handle loop 166.

The ends 158, 160 of the hinge side handle 150 are permanently attached through the slots 110 of the hinge base mounting brackets 100a, 100b and the ends 158, 160 of the latch side handle 152 are permanently attached through the slots 110 of the latch base mounting brackets 100e, 100f. Rivets 164 are also used to attach the handles 150, 152 to the base 22 and lid 24 to help alleviate strain on the stitching 162. Preferably, the manner of attaching the rivets makes the attachment resistant to liquid passing through.

Figure 5:
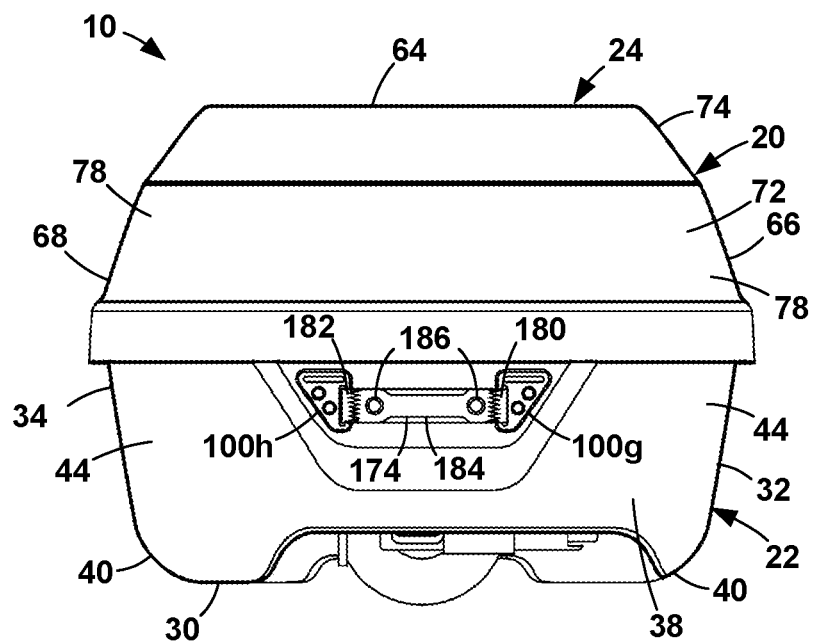
FIG. 5 is an elevational view of the handle end of the bag in the work orientation.
Figure 6:
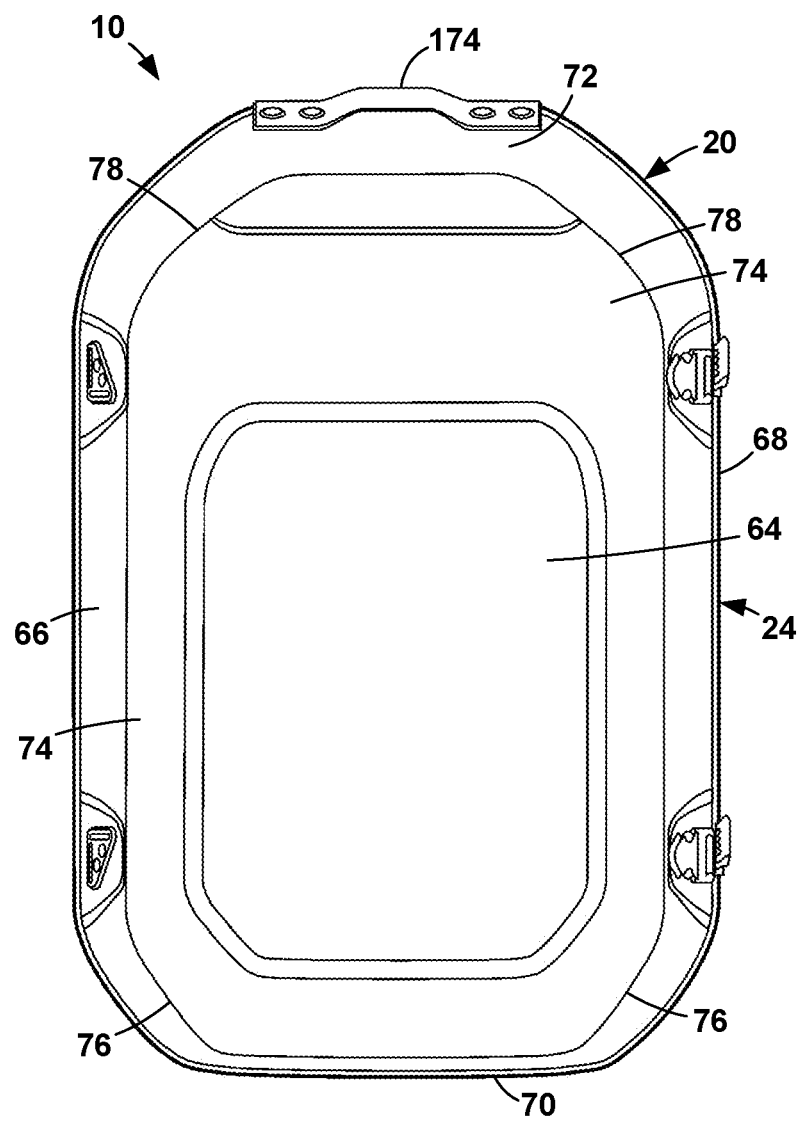
FIG. 6 is an elevational view of the top of the bag in the upright-carry orientation.
Figure 7:
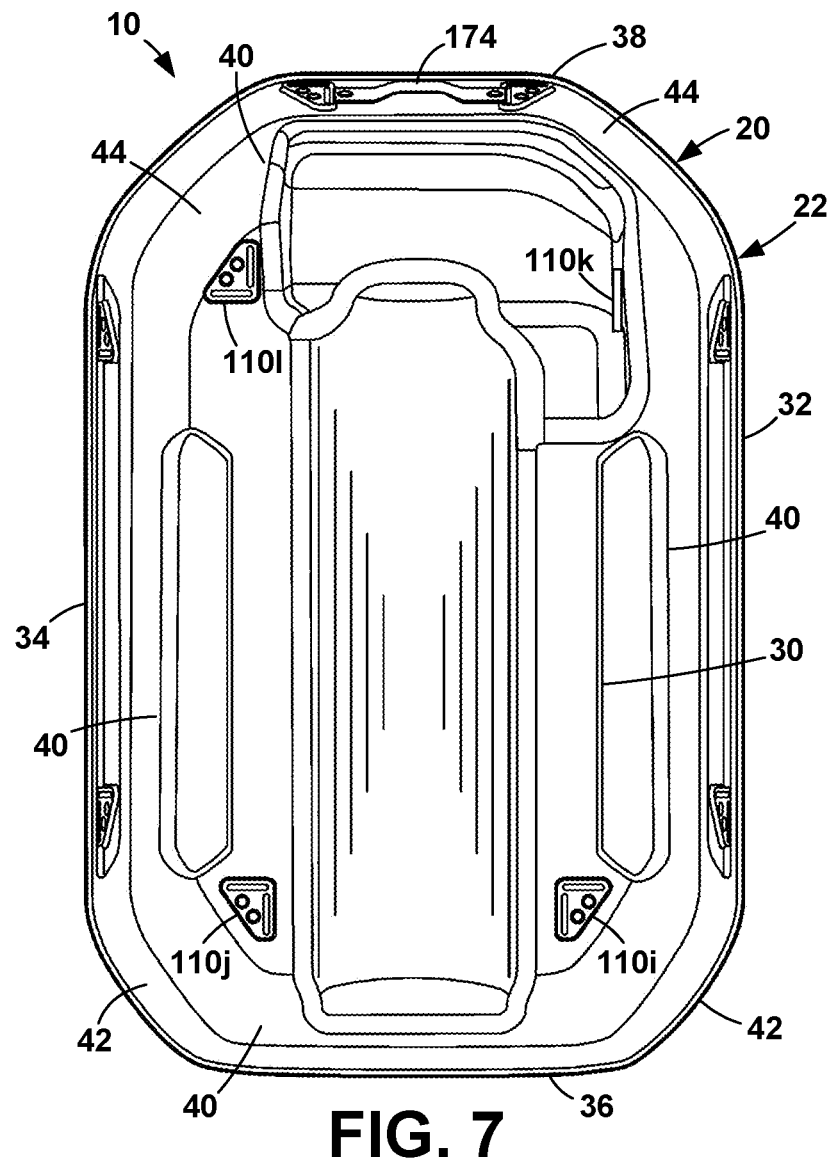
FIG. 7 is an elevational view of the bottom of the bag in the upright-carry orientation.
Figure 8:
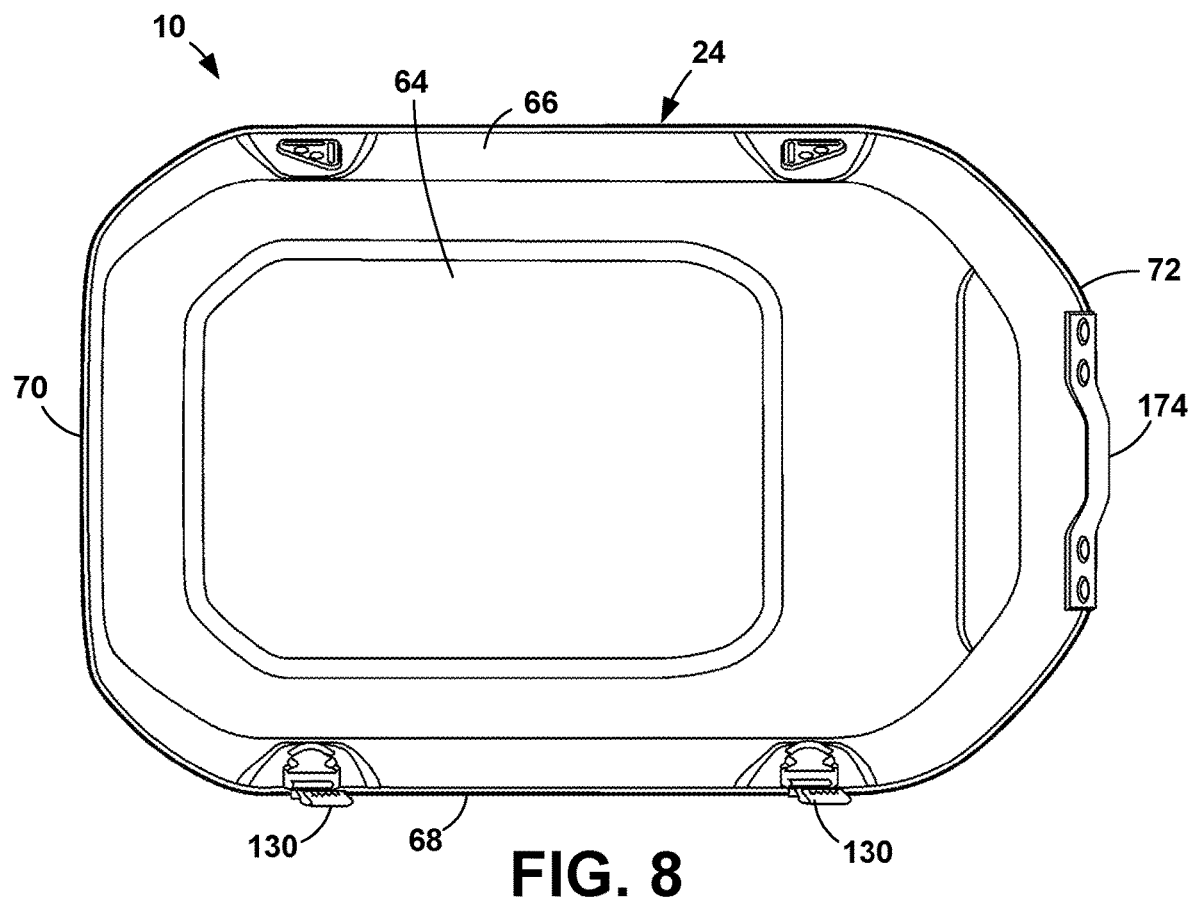
FIG. 8 is an elevational view of the top of the bag in the side-carry orientation.
Figure 13:
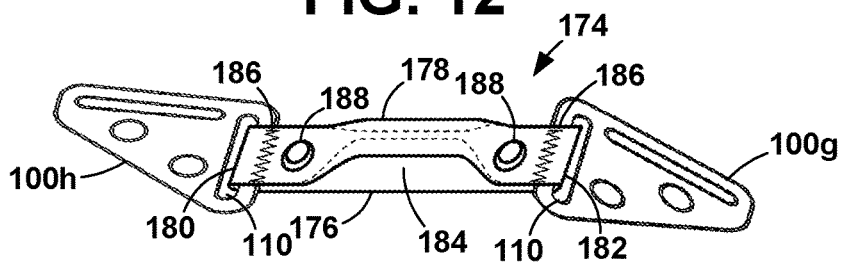
FIG. 13 is a detail view of the end handle.

The handle end handle 174, shown in FIGS. 5 and 13, is composed of a base strap 176 and loop strap 178, each of which is composed of a polyester or nylon webbing coated with a PU, TPU, or PVC for durability and to facilitate cleaning. The ends 180, 182 of the handle end handle 174 are permanently attached through the slots 110 in the handle base mounting brackets 100g, 100h in such a way as to form an elongated, longitudinal handle loop 184. Rivets 186 are also used to attach the handle 174 to the base 22 to help alleviate strain on the end attachment. Preferably, the manner of attaching the rivets makes the attachment resistant to liquid passing through.

The handles 150, 152, 174 are attached to the base 22, rather than the lid 24, because of how the oxygen cylinder 12, described below, unbalances the bag 10.

The bag 10 can be manually carried by a handle loop 166, 184. Carabiners can be inserted through the carabiner loops 168 to hang the bag 10 from a gurney or other platform in the side-carry orientation.

Figure 14:
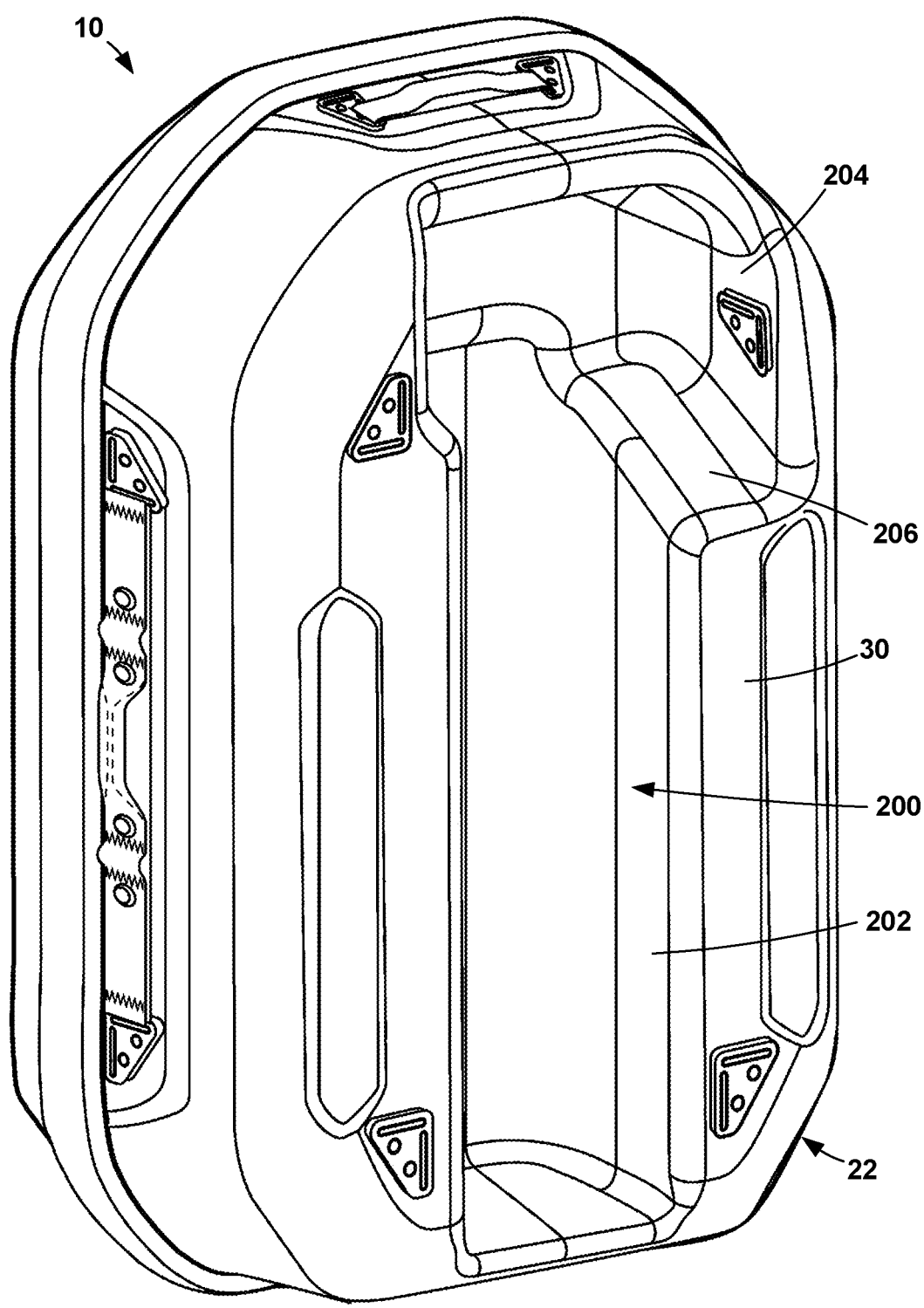
FIG. 14 is a bottom, perspective view of the closed bag with a cylinder recess.
Figure 15:
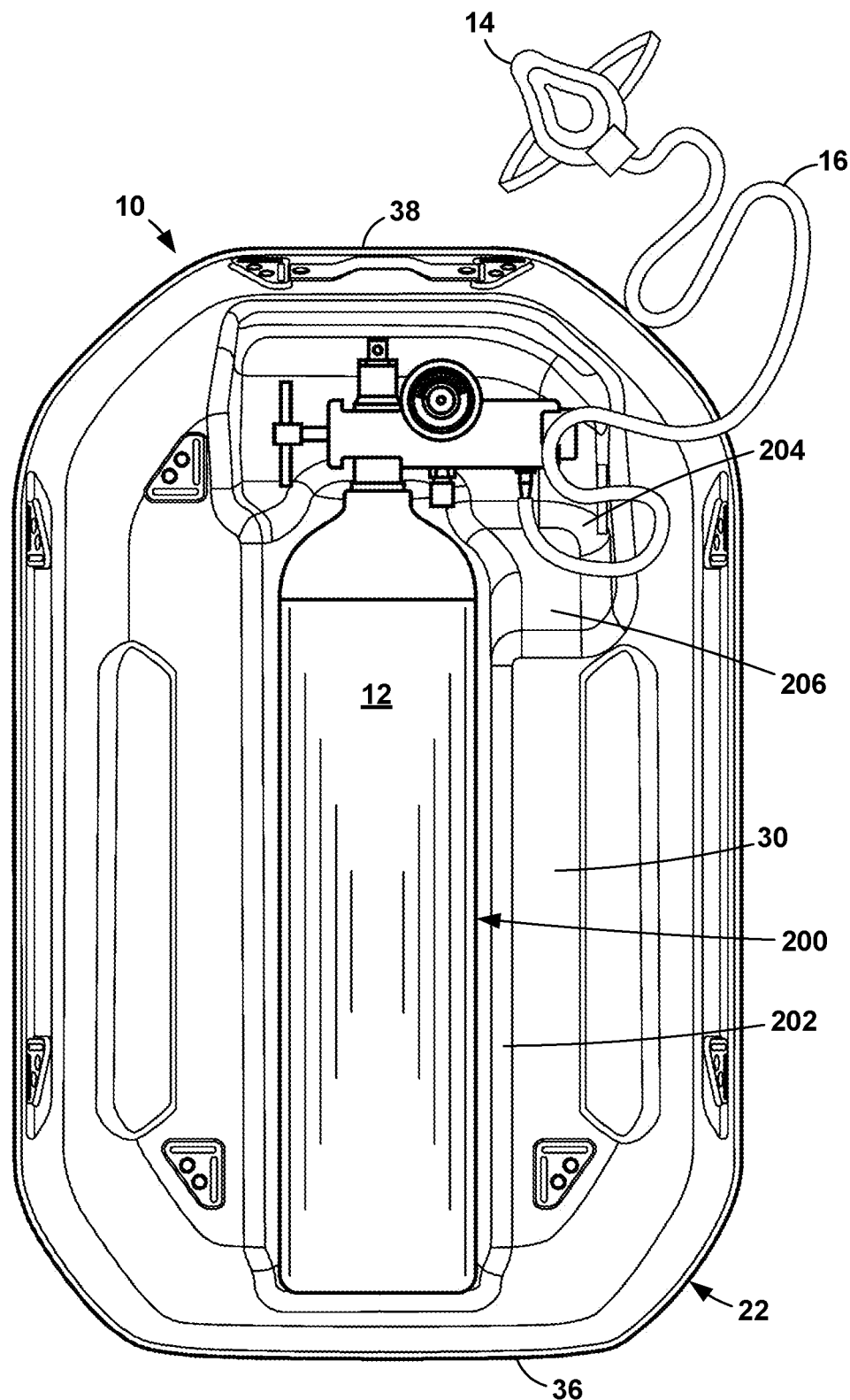
FIG. 15 is a bottom view of the bag with a cylinder in the cylinder recess.

As shown in FIGS. 14 and 15, the base floor 30 optionally has a recess 200 extending into the compartment 26 for holding an oxygen cylinder 12 with an attached regulator 14. Unless otherwise indicated, the description assumes that the bag 10 is in the end carry orientation. The recess 200 extends longitudinally between the foot end 36 and the handle end 38 and approximately parallel to the hinge side 32 and latch side 34. Preferably, the recess 200 is sized to except both M9 and M15 cylinders, which are 11 cm in diameter, and 36 cm and 50 cm, respectively, in height including the regulator. The cylinder 12 itself fits into the longitudinal portion 202 of the recess 200. The regulator 14 extends laterally into a niche 204 off the longitudinal portion 202. The inner wall 206 of the niche 204 is sloped toward the foot end 36 so that the hose 16 extending from the regulator 14 does not have to bend too sharply.

Figure 16:
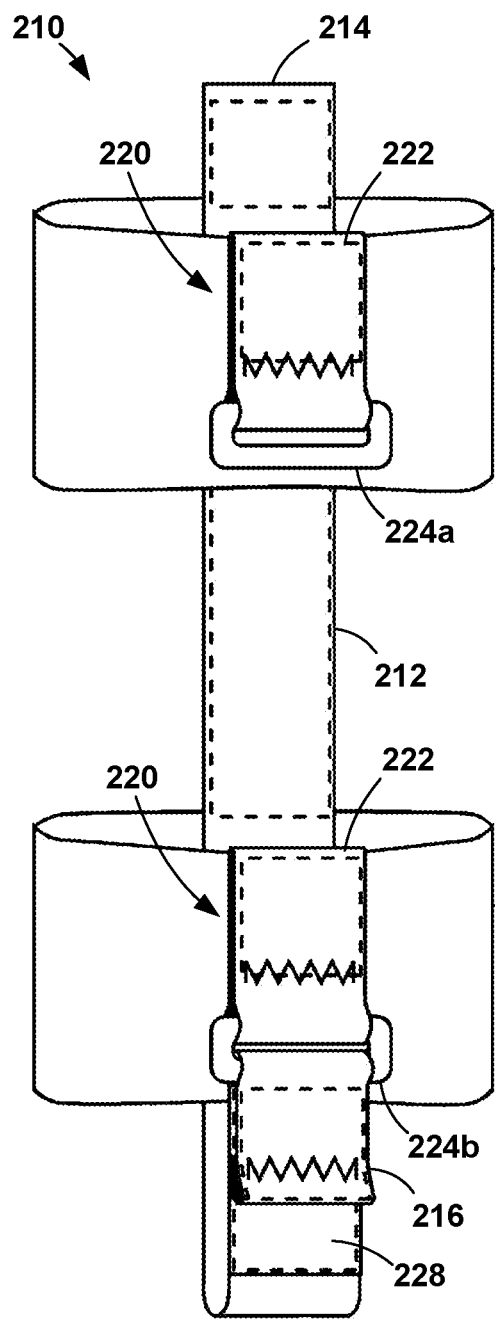
FIG. 16 is a detail view of the cylinder harness.

The cylinder 14 is retained in the recess 200 by a cylinder harness 210, shown in FIG. 16. The harness 210 has a polyester or nylon web base strap 212 with a bare end 214 and a microhook fastener 216 at the other end. The section of the base strap 212 at the bare end 214 is riveted to the base 22 within the recess 200 such that the base strap microhook fastener 216 hangs downwardly.

At least one and preferably a pair of wide, circular, elastic bands 218a, 218b (collectively, 218) are attached to the base strap 212 so that the axis of the bands 218 are parallel to the strap 212 and that they are spaced from each other. The diameter of the bands 218 is sized to accept and retain M9 and M15 cylinders. A sizing strap 220 is attached to each band 218 opposite to where the band 218 is attached to the base strap 212. The sizing strap 220 has a bare end 222 and a square ring 224a, 224b (collectively, 224) at the other end. The section of the sizing strap 220 at the bare end 222 is stitched to the band 218 such that the sizing strap ring 224 hangs downwardly.

Figure 17:
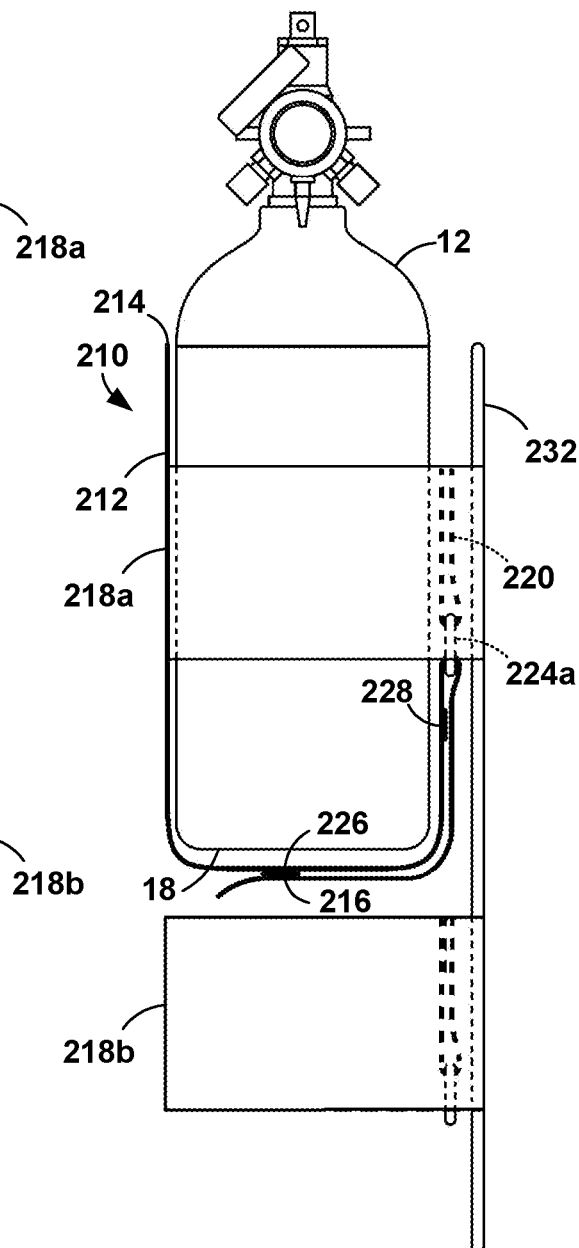
FIG. 17 is a side view of the cylinder harness with an M9 cylinder.

As shown in FIG. 17, the M9 cylinder 12 is installed in the harness 210 by inserting it into the upper band 218a until the regulator 16 is within the regulator niche 204. The base strap microhook fastener 216 is inserted and pulled through the upper ring 224a until the base strap 212 is snug against the bottom 18 of the cylinder 12. The microhook fastener 216 is pressed against an M9 microloop fastener 226 on the base strap 212.

Figure 18:
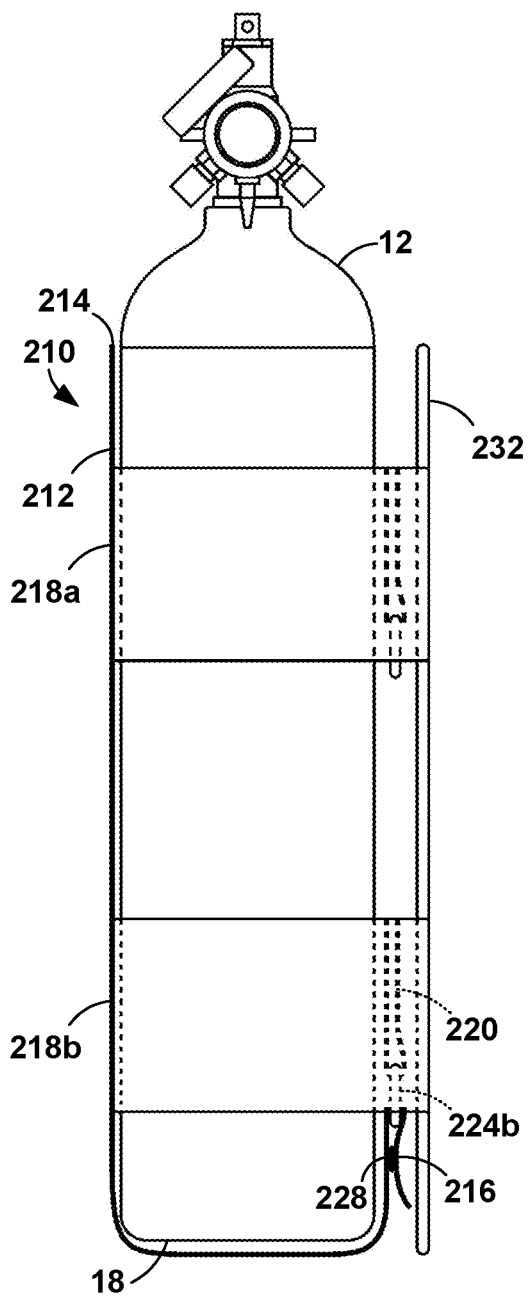
FIG. 18 is a side view of the cylinder harness with an M15 cylinder.

As shown in FIG. 18, the M15 cylinder 12 is installed in the harness 210 by inserting it into the upper band 218a and the lower band 218b until the regulator 16 is within the regulator niche 204. The base strap microhook fastener 216 is inserted and pulled through the lower ring 224b until the base strap 212 is snug against the bottom 18 of the cylinder 12. The microhook fastener 216 is pressed against an M15 microloop fastener 228 on the base strap 212.

Figure 19:
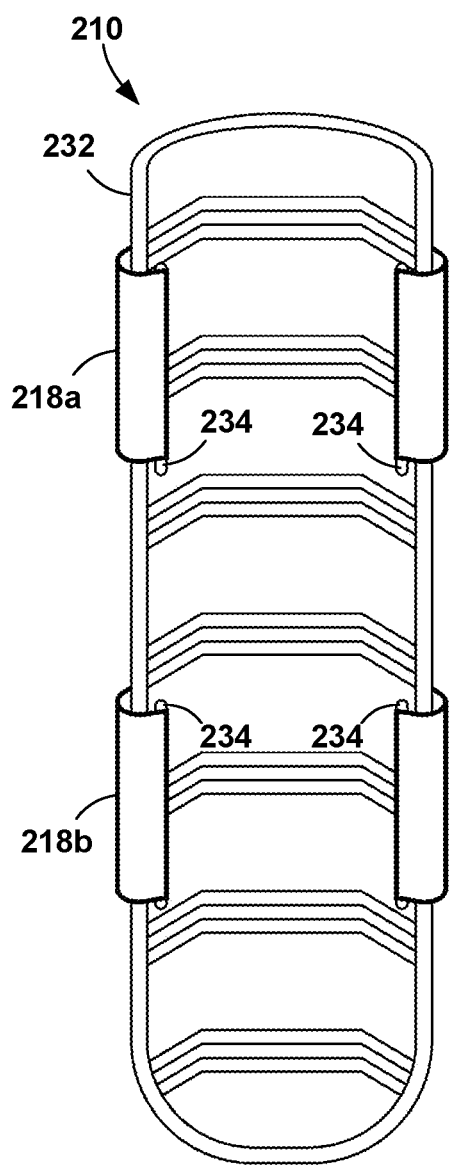
FIG. 19 is a detail view of the cylinder harness with a foam pad.

Optionally, a foam pad 232 is attached to the harness 210 to protect the wearer's back from the cylinder 12. The pad 232 has slots 234 through which the bands 218 extend, as in FIG. 19.

The bag 10 includes a waist belt 240, a pair of shoulder straps 242a, 242b (collectively, 242), and a carry strap 244. All of these components are detachably attached to the base 22 so that they can be removed to facilitate cleaning. Optionally, the bag 10 comes with multiple sets of these components so they can be swapped out after each job to await cleaning. Optionally, these components are disposable.

Figure 20:
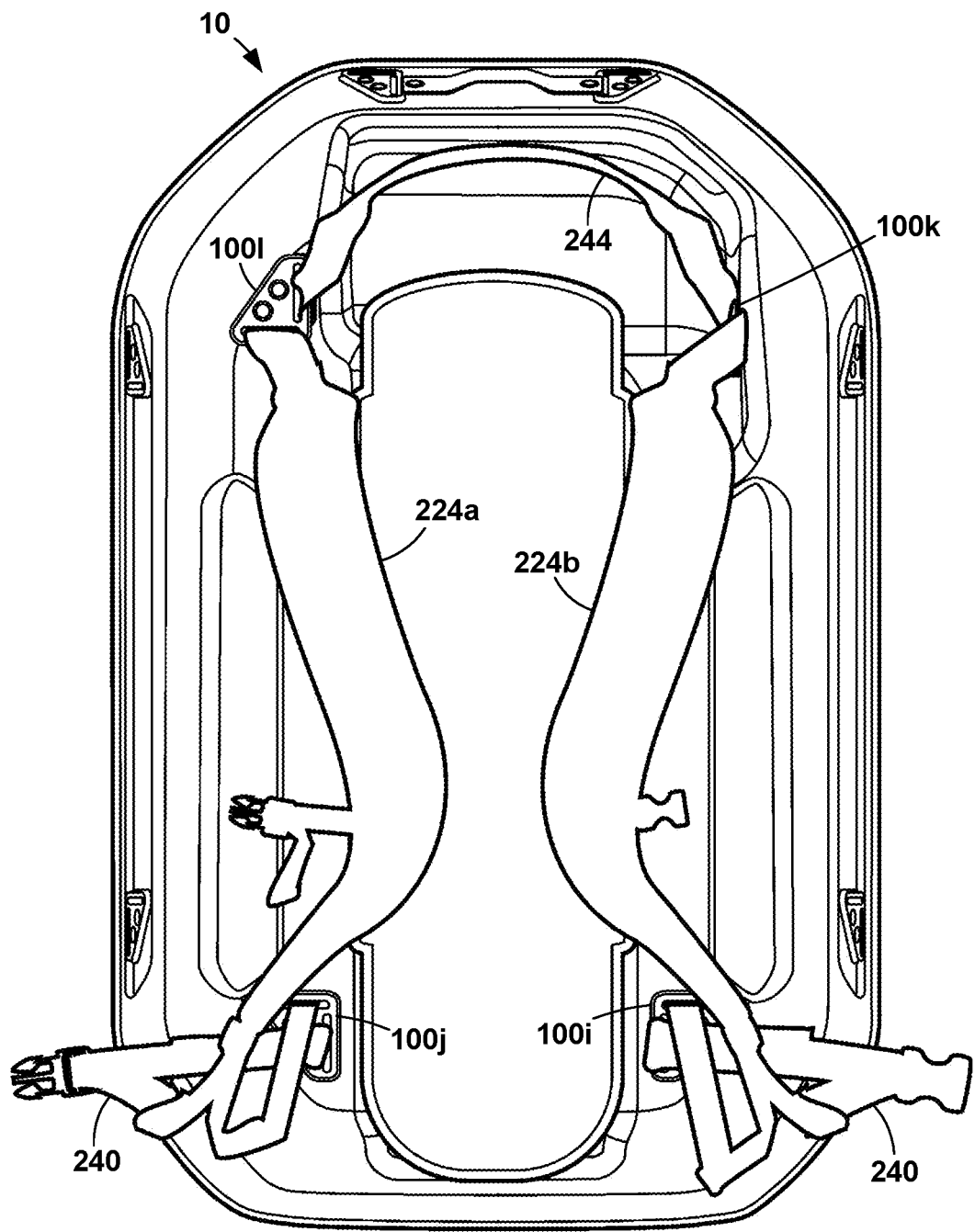
FIG. 20 is a view of the bottom of the bag in the upright-carry orientation with a cylinder recess, shoulder straps, waist straps, and carry strap.
Figure 21:
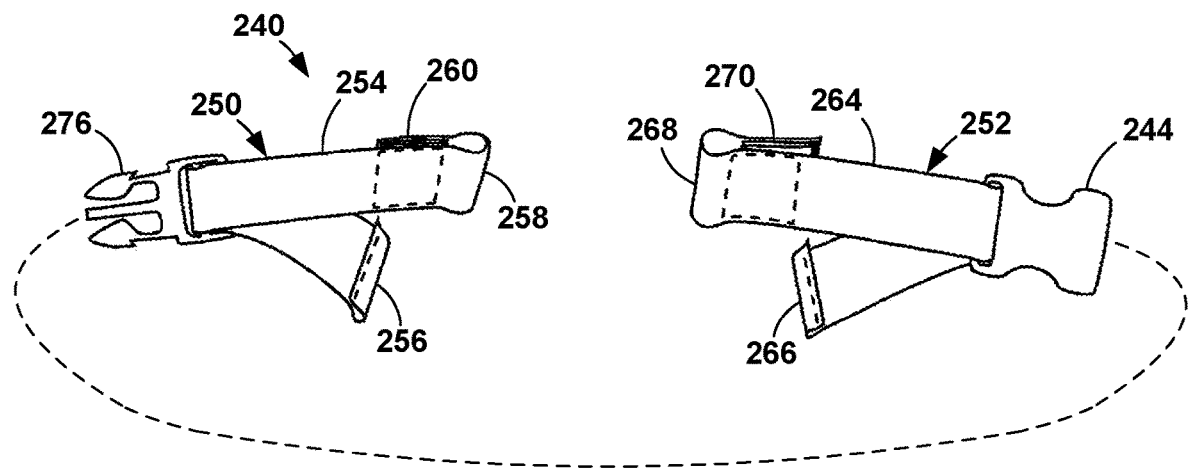
FIG. 21 is a detail view of the waist belt.

As shown in FIGS. 20 and 21, with the bag 10 in the end carry orientation, the waist belt 240 has a right-side component 250 and a left side component 252. The right-side component 250 is removably attached to the base 22 by a lower right bracket 100j and the left side component 252 is removably attached to the base 22 by a lower left bracket 100i. The right-side component 250 has a nylon web strap 254 with a free end 256 and an attachment end 258 with a hook/loop foldback fastener 260. The attachment end 258 is inserted through the right lower bracket slot 110 and folded back until the fastener 260 engages. The left side component 252 has a nylon web strap 264 with a free end 266 and an attachment end 268 with a hook/loop foldback fastener 270. The attachment end 268 is inserted through the left lower bracket slot 110 and folded back until the fastener 270 engages. The waist belt components 250, 252 are removed from the bag 10 by disengaging the fasteners 260, 270 and pulling the straps 254, 264 from the brackets 100i, 100j.

The right-side component 250 and left side component 252 are detachably attached to each other by a side-release buckle 274. The buckle male component 276 is on one of the right-side components 240 or left side components 242 and the female component 278 is on the other side component. The buckle components 276, 278 are attached to be adjustable along the length of the waist belt component 250, 252.

Figure 22:
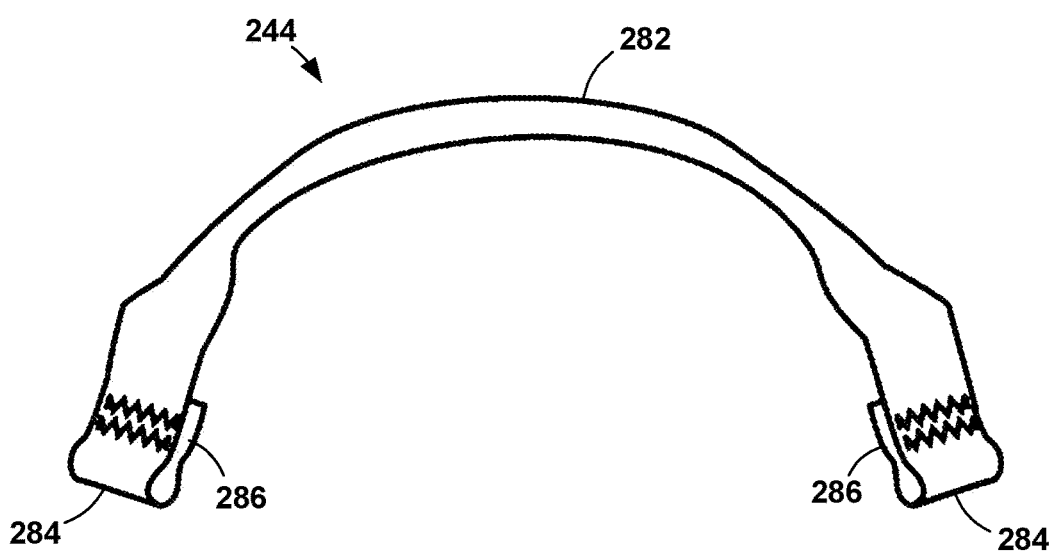
FIG. 22 is a detail view of the carry strap.

The carry strap 244 can be used to carry the bag 10. The carry strap 244 is removably attached to the base 22 by an upper right bracket 100k and an upper left bracket 100l. As shown in FIG. 22, the carry strap 244 is a nylon web strap 282 with a hook/loop foldback fastener 286 at each end 284. The end 284 is inserted through the associated upper bracket slot 110 and folded back until the fastener 286 engages. The carry strap 244 is removed from the bag 10 by disengaging the fasteners 286 and pulling the ends 284 from the brackets 100k, 100l.

The pair of shoulder straps 242a, 242b can be used as a hands-free way to carry the bag 10. The shoulder straps 242a, 242b, shown in FIG. 23, have a padded section 290 with a top attaching strap 296 at the top end 292 and a bottom attaching strap 298 at the bottom end 294.

The right and left shoulder strap top attaching straps 296 are attached to the base 22 at the upper right bracket 100k and upper left bracket 100l, respectively. The top attaching strap 296 includes a short strip 300 of nylon web material that is sewn to the padded section 290, as at 302. The other end 304 of the strip 300 is threaded through a square ring 306, through the appropriate attachment bracket slot 110, and back through the square ring 306 in a manner known in the art.

The bottom attaching strap 298 includes a short strip 310 of nylon web material that is sewn to the padded section 290, as at 312. The other end of the strip 310 is attached to a ladder lock slider 314. The bottom attaching strap 298 further includes an adjusting strap 316 that is attached to the strip 310 by extending through the ladder lock slider 314 in a manner known in the art. One end of the adjusting strap 316 is formed into a loop 318.

The right and left shoulder strap bottom attaching straps 298 are attached to the base 22 at the lower right bracket 100i and lower left bracket 100j, respectively. The other end 320 of the adjusting strap 316 is inserted through the appropriate lower bracket slot 110 then folded back and threaded through a square ring buckle 322 for attachment.

Figure 23:
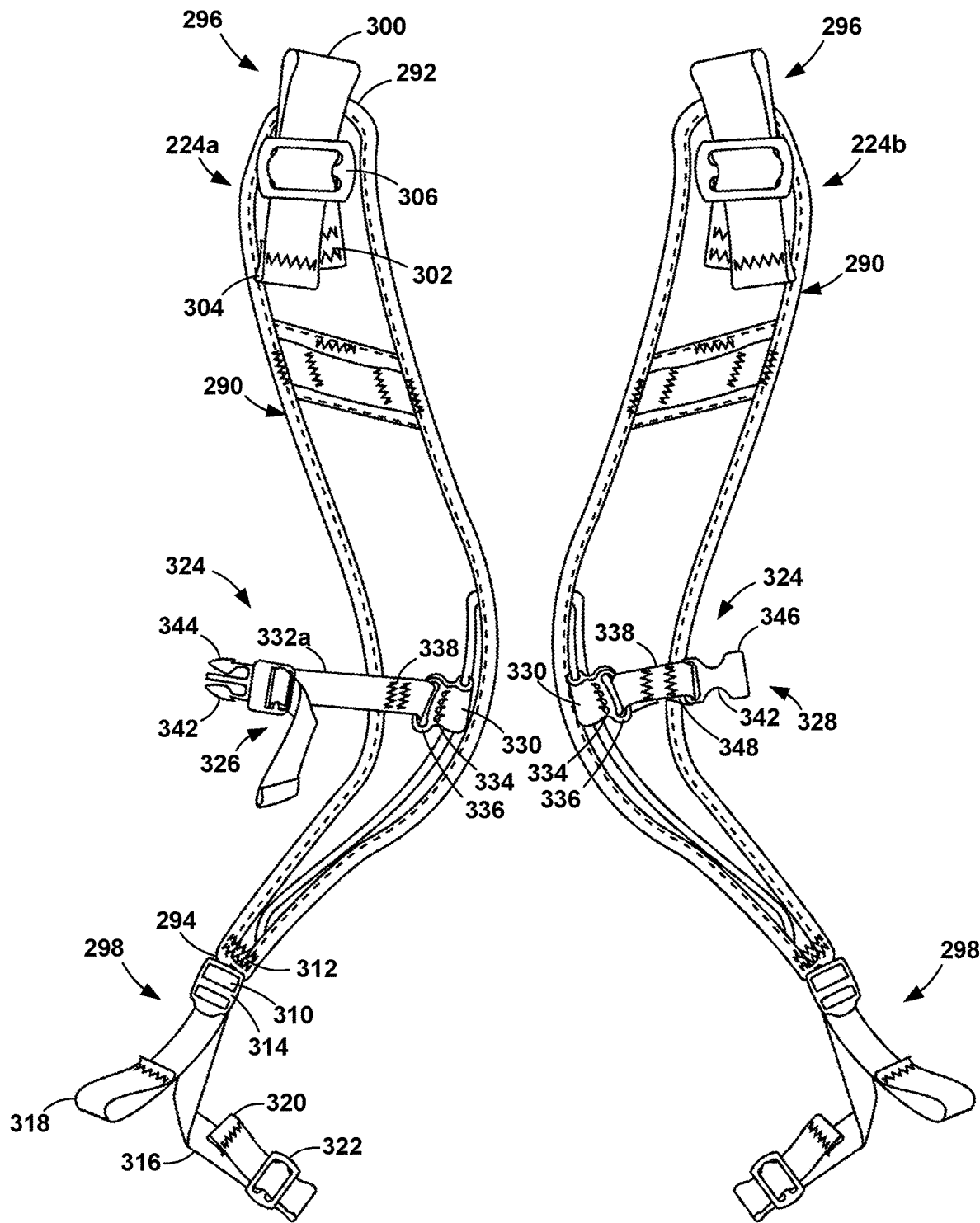
FIG. 23 is a detail view of the shoulder straps.
Figure 24:
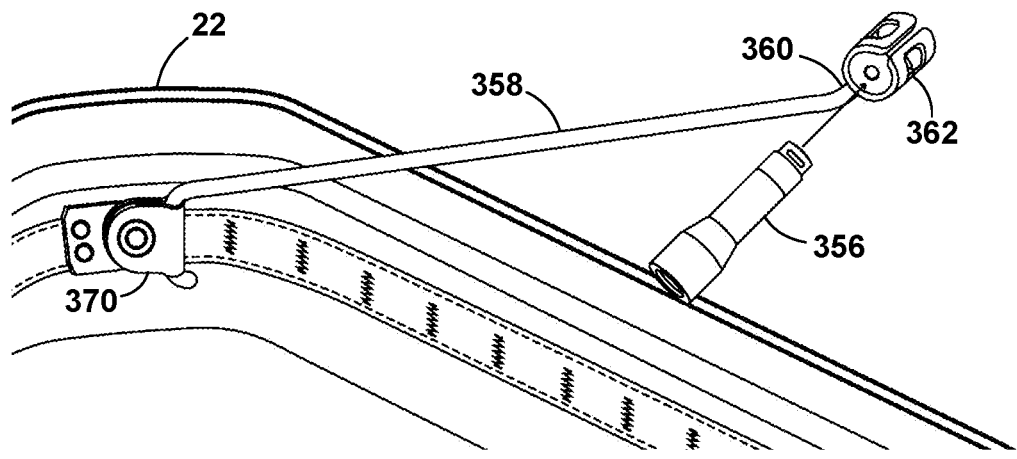
FIG. 24 is a detail view of the flashlight arm.
Figure 25:
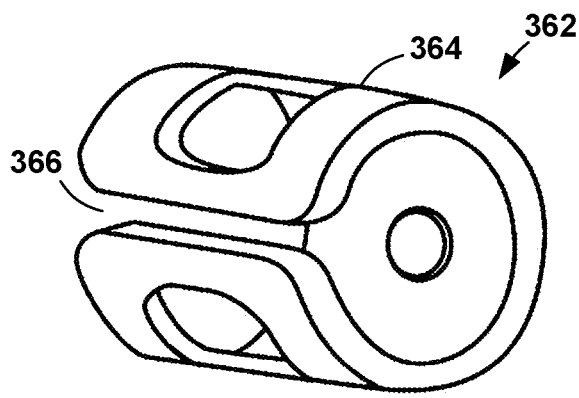
FIG. 25 is a detail view of the flashlight arm bracket.
Figure 26:
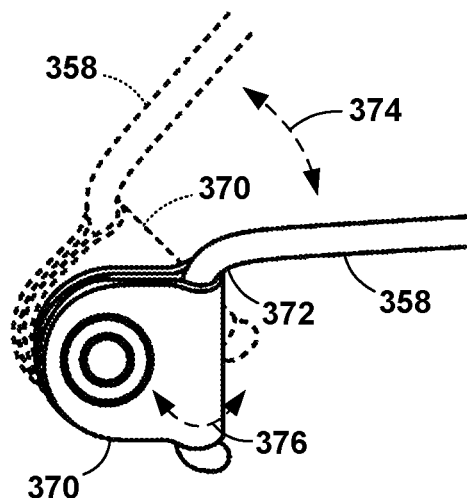
FIG. 26 is a detail view of the flashlight arm mount.

As shown in FIG. 23, the chest belt 324 has a right-side component 326 and a left side component 328. Each of the components has an attachment strap 330 and a buckle strap 332a, 332b (collectively, 332), both of which are composed of nylon webbing. One end of the attachment strap 330 is sewn to the padded section 290, as at 334. The other end of the attachment strap 330 has a square ring 336. The buckle strap 332 extends through the ring 336, is folded back and sewn, as at 338.

The right-side component 326 and left side component 328 are detachably attached to each other by a side-release buckle 342. The buckle male component 344 is on one of the right buckle strap 332a or left buckle strap 332b and the female component 346 is on the other side buckle strap. The male buckle component 344 is attached to be adjustable along the length of the buckle strap 332 in a manner known in the art. The female component 346 is attached by a loop 348 at the end of the buckle strap 332.

Optionally, the bag 10 includes a movable arm 358, shown in FIGS. 9 and 24-26, to which a flashlight 356 can be attached. The flashlight 356 removably attaches to the arm 358 at a bracket 362 attached to the free end 360 of the arm 358. The bracket 362 is a cylindrical tube 364 with a paraxial slot 366 in the wall. The slot 366 permits the tube 364 to stretch in diameter enough to slide the bracket 362 over the flashlight 356. The bracket 362 holds the flashlight 356 by clamping around the flashlight 356.

The arm 358 attaches to the bag 10 inside the base 22. A clamp 370 holds the mounted end 372 of the arm 358 so that the arm 358 can rotate, as at 374, and pivot, as at 376.

As shown in FIG. 9, the lid 24 optionally includes a divider 406 generally parallel to the lid sides 66, 68 that separates the lid 24 into two compartments 408. Optionally, the divider 406 is removable by using, for example, snaps, magnetic strips, or hook and loop fasteners. The method used for attachment needs to be relatively robust so that the divider 406 does not detach during use. The divider 406 is preferably composed of polyester or nylon with a PU, TPU, or PVC coating.

Figure 27:
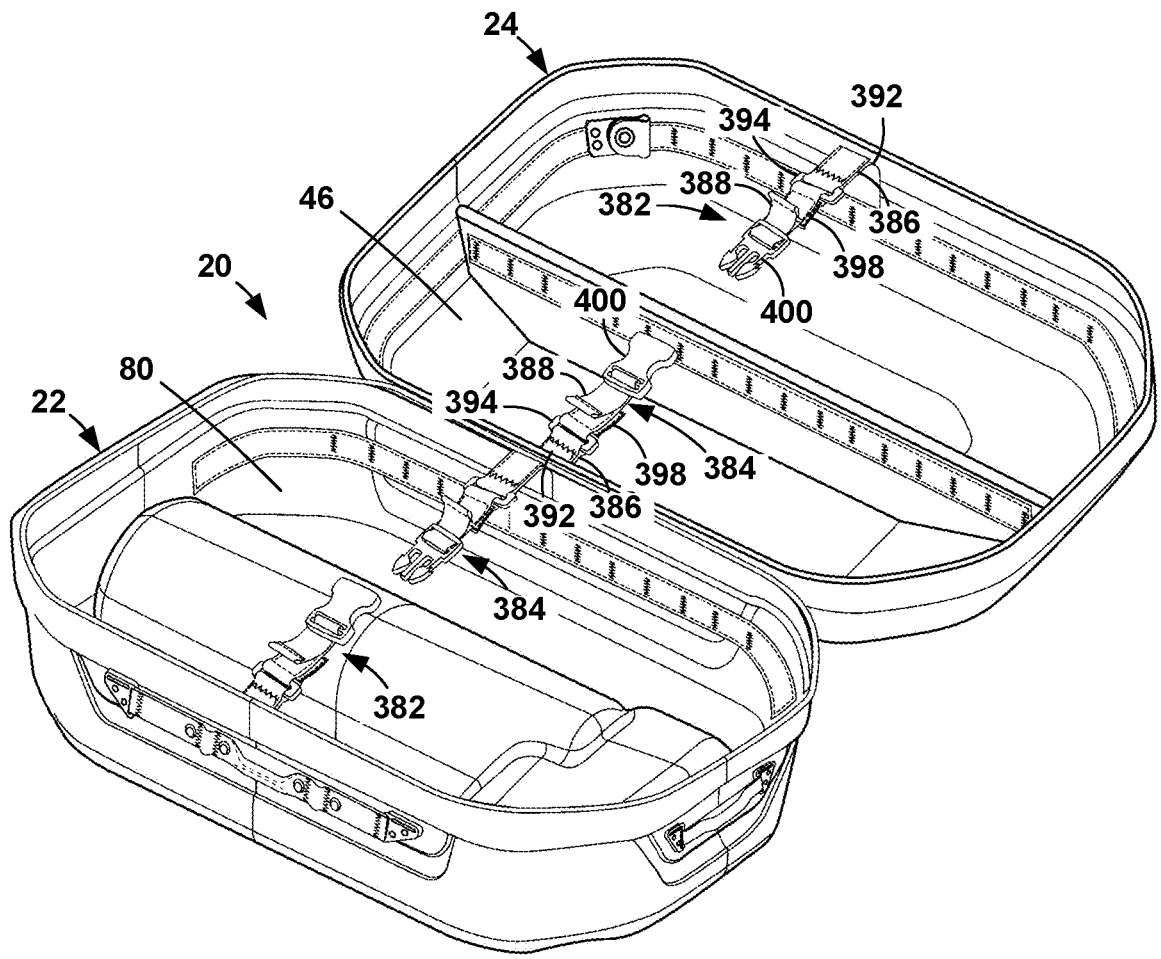
FIG. 27 is a perspective view of the bag in the opened position with optional compression straps.

As shown in FIG. 27, optional compression straps 382, 384 extend from the hinge side 66 and the latch side 68 of the base 22 and lid 24. Each compression strap 382, 384 as two parts, the attachment strap 386 and the buckle strap 388. The straps 386, 388 are polyester or nylon web straps that are coated with PU, TPU, or PVC for durability and to facilitate cleaning.

The attachment strap 386 has one end 392 permanently attached to the lid 24 by rivets. At the other end has a square ring 394. The buckle strap 388 has a hook/loop foldback fastener 398 at one end. The foldback fastener 398 is inserted through the ring 394 and folded back until the fastener 398 engages. The other end of the buckle strap 388 has the male or female component of a side-release buckle 400. The buckle components 400 are attached to the buckle strap 388 so that the lengths of the compression straps 382, 284 are adjustable by means well-known in the art.

As shown in FIG. 9, strips 420 of Pouch Attachment Ladder System (PALS) webbing are attached to the inside surface of the base 22 and lid 24. The base 22 has PALS strips 420 on the base hinge side 32 and base latch side 34 parallel to the base lip 52. The lid 24 has PALS strips 420 on the lid hinge side 66 and lid latch side 68 parallel to the lid lip 86. The divider 406 has PALS strips 420 on the hinge side 410 and latch side 412 parallel to the divider top edge 414. The PALS strips 420 extend the length of their respective surfaces. The PALS strips 420 can be a single strip, as in FIG. 9, or a pair of parallel strips, as in FIG. 28.

Figure 28:
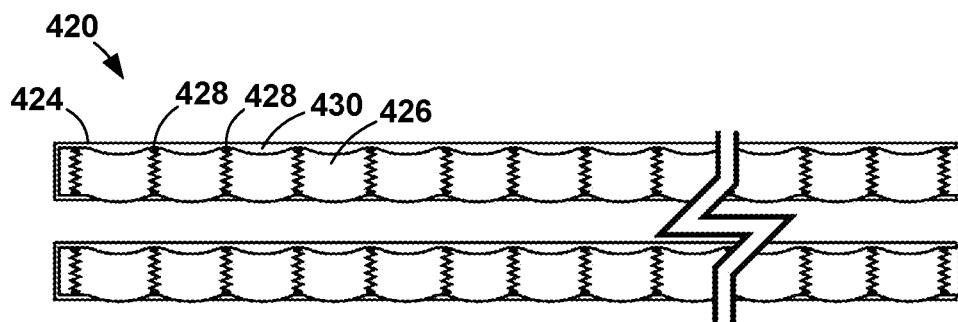
FIG. 28 is a front view of a PALS strip.
Figure 29:
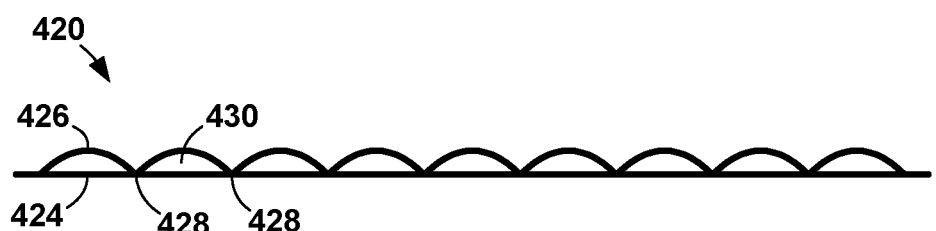
FIG. 29 is a top view of a PALS strip.

As shown in FIGS. 28 and 29, the PALS strips 420 are composed of two parallel nylon or PVC webs, a backing strip 424 and a loop strip 426, each one inch wide. The loop strip 426 is bartacked to the backing strip 424 at 1.5-inch intervals, as at 428, such that the loop strip 426 is spaced from the backing strip 424 between bartacks 428, as at 430. The bartacking can be by any means that retains the strips 424, 426 together. For example, fabrics can be stitched, and PVC can be welded or glued.

The PALS strips 424 are attached to the base/lid/divider by an adhesive or weld on the backing strip 424 and/or by rivets.

Figure 30:
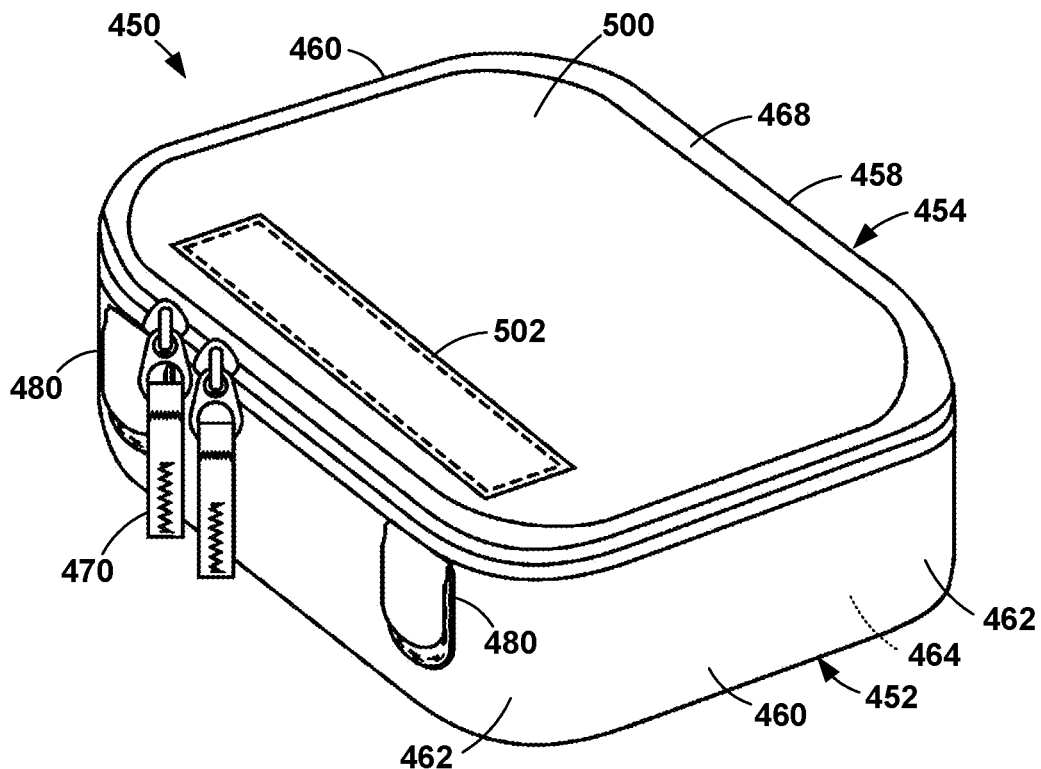
FIG. 30 is a perspective view of a closed caddy.
Figure 31:
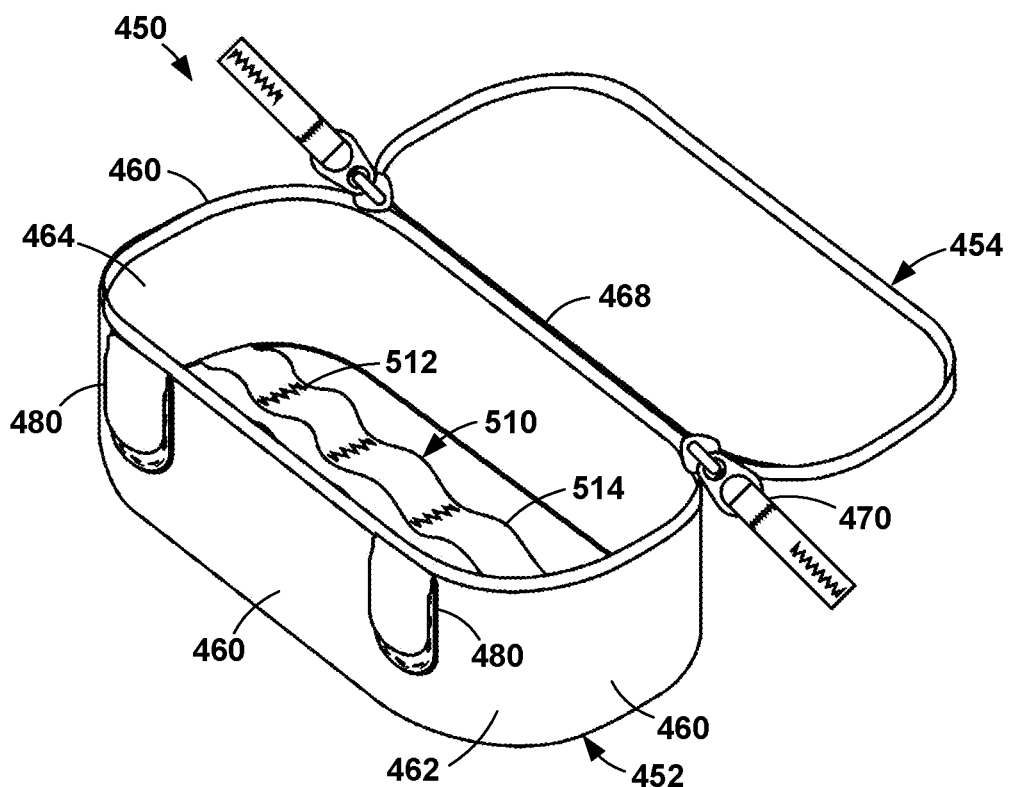
FIG. 31 is a perspective view of an open caddy.

The bag 10 of the present invention includes caddies 450 of various sizes that are removably affixed to the inside of the bag 10. As shown in FIGS. 30-32, each caddy 450 has a base 452 and a cover 454. The base 452 has a floor 456 and four sides 458, 460 with optional rounded corners, as at 462, forming a compartment 464 within. The cover 454 is essentially flat and that, when mated with the top edge 466 of the base 452, forms a ceiling that closes the compartment 464. The base 452 and cover 454 are attached at one side 458 by a living hinge 468. A closure 470 attaches the other three sides 460 to the base 452 to secure the compartment 464 closed. Preferably, as shown in FIGS. 30-32, the closure 470 is a zipper.

The caddy 450 is composed of a polyurethane or PVC tarp with sewn seams. Preferably, the caddy 450 is composed of a clear material so that the contents can be seen without having to open the caddy 450.

The caddy 450 has top, bottom, and side seams, typically of regular thread. The caddy 450 is not totally cleanable as is the rest of the bag but are made inexpensively and can be disposed of in the medical waste stream.

The caddies 450 are removably affixed in the bag 10 by the PALS strips 420. Each caddy 450 has several fold over tabs 480 mounted to opposed sides 458, 460 of the caddy 450. Each side with tabs 480 has a tab 450 at each end spaced apart by an integer multiple of the PALS strip loop spacing 430.

As shown in FIGS. 33 and 34, each tab 480 is a fabric strip, the bottom portion 482 of which is sewn to the caddy side 458, 460. The bottom portion 482 has a steel washer 494 attached to it. The top portion 484 has a magnet 492 attached to it. The top portion 484 folds downwardly at a fold 486 to overlap the bottom portion 483 such that the magnet 492 overlaps the washer 494 to latch the top portion 484 to the bottom portion 482. To use, the top portion 484 is inserted through a PALS strip loop 430 and folded over until the magnet 492 latches to the washer 494. The PALS loop strip 426 is secured between the top portion 484 and the bottom portion 482.

Optionally, the outside surface 500 of the cover 454 has a label 502 composed of a woven material that is sewn onto the cover 454. The label 502 preferably has a black background and high-visibility yellow artwork on top of the background. The artwork can include text and/or figures. The artwork must be clearly readable and so is preferably at least 2 cm high with the background at least 3.1 cm high. Optionally, the artwork is a plain surface that can be manually written on with a permanent marker.

Optionally, elastic strips 510 are sewn to the base floor 456. The strips 510 are sewn laterally, as at 512, to form loops 514 into which items can be inserted.

Figure 35:
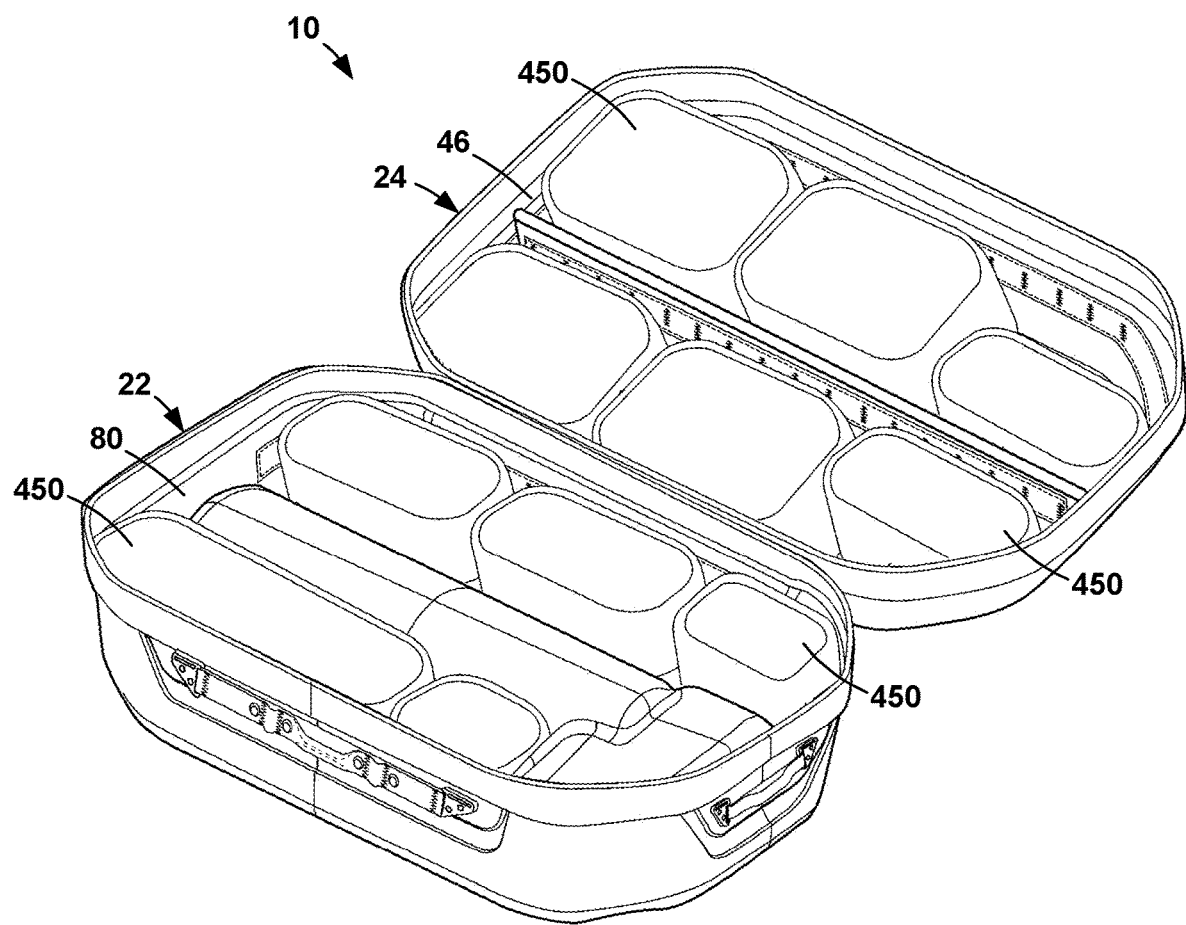
FIG. 35 is a perspective view of the bag with caddies.

As mentioned above, the caddy 450 comes in several sizes. They are sized so that a number of them can fit within the bag 10 at the same time, as in FIG. 35. In the current design, there are three sizes: (1) 15 cm long by 12 cm wide by 10 cm high, (2) 18 cm long by 12 cm wide by 10 cm high, and (3) 18 cm long by 18 cm wide by 10 cm high.

Thus, it has been shown and described a carry bag. Since certain changes may be made in the present disclosure without departing from the scope of the present invention, it is intended that all matter described in the foregoing specification and shown in the accompanying drawings be interpreted as illustrative and not in a limiting sense.

The invention claimed is:

1. A carry bag comprising:
   (a) a base composed of a liquid-impermeable material with a floor, a base hinge side, a base handle side opposite the base hinge side, a base foot end between the base hinge side and base handle side, and a base handle end opposite the base foot end, all forming a base compartment with a base circumferential lip, the floor having a cylinder recess extending into the base compartment and extending approximately parallel to the base hinge side and base handle side, the cylinder recess being adapted to removably accept a gas cylinder with a regulator;
   (b) a lid composed of a liquid-impermeable material with a roof, a lid hinge side, a lid handle side opposite the lid hinge side, a lid foot end between the lid hinge side and lid handle side, and a lid handle end opposite the lid foot end, all forming a lid compartment with a lid circumferential lip;

(c) hinges pivotally attaching the lid hinge side to the base hinge side, each hinge being a flexible hinge webbing permanently attached to the base and lid;

(d) at least one latch for latching the lid to the base when engaged, each of the at least one latch having a female component and a male component, the female component permanently attached to the base latch side or the lid latch side, the male component being attached to a flexible latch webbing that is permanently attached to the base latch side or the lid latch side;

(e) the base circumferential lip and lid circumferential lip engaging to form a liquid-resistant seal when the at least one latch is engaged;

(f) whereby all non-removable components of the case are composed exclusively of materials that are cleanable with bleach or hospital-grade wipes.

2. The carry bag of claim 1 wherein the base and lid are composed of an emulsified ethylene-vinyl acetate copolymer.

3. The carry bag of claim 1 wherein the hinge webbing is attached by hinge mounting brackets and the latch webbing is attached by a latch mounting bracket.

4. The carry bag of claim 3 wherein the mounting brackets are powder-coated or anodized aluminum.

5. The carry bag of claim 1 wherein the male component of the latch is adjustably attached to the latch webbing.

6. The carry bag of claim 1 wherein the hinge and the latch webbings are polyester or nylon.

7. The carry bag of claim 1 wherein the hinge and latch webbings are coated with a polyurethane, thermoplastic polyurethane, or polyvinyl chloride.

8. The carry bag of claim 1 further comprising PALS strips on the inside surface of the base hinge side, base latch side, lid hinge side, and lid latch side, and a plurality of caddies removably attachable to the PALS strips.

9. The carry bag of claim 1 further comprising a divider in the lid generally parallel to the lid hinge side and lid latch side, the divider having PALS strips thereon, the PALS strips composed of nylon or polyvinyl chloride webbing.

10. The carry bag of claim 9 wherein the divider is removable.

11. The carry bag of claim 1 further comprising removable shoulder straps.

12. The carry bag of claim 1 further comprising a cylinder harness including a strap permanently attached to the case in the cylinder recess and at least one elastic band adapted to extend around the gas cylinder.

13. A carry bag comprising:

(a) a base composed of a emulsified ethylene-vinyl acetate copolymer with a floor, a base hinge side, a base handle side opposite the base hinge side, a base foot end between the base hinge side and base handle side, and a base handle end opposite the base foot end, all forming a base compartment with a base circumferential lip, the floor having a cylinder recess extending into the base compartment and extending approximately parallel to the base hinge side and base handle side, the cylinder recess being adapted to removably accept a gas cylinder with a regulator;

(b) a lid composed of a emulsified ethylene-vinyl acetate copolymer with a roof, a lid hinge side, a lid handle side opposite the lid hinge side, a lid foot end between the lid hinge side and lid handle side, and a lid handle end opposite the lid foot end, all forming a lid compartment with a lid circumferential lip;

(c) hinges pivotally attaching the lid hinge side to the base hinge side, each hinge being a polyester or nylon hinge webbing permanently attached to the base and lid by hinge mounting brackets;

(d) at least one latch for latching the lid to the base when engaged, each of the at least one latch having a female component and a male component, the female component permanently attached to the base latch side or the lid latch side, the male component being attached to a polyester or nylon latch webbing that is permanently attached to the base latch side or the lid latch side by a latch mounting bracket;

(e) the base circumferential lip and lid circumferential lip engaging to form a liquid-resistant seal when the at least one latch is engaged;

(f) PALS strips on the inside surface of the base hinge side, base latch side, lid hinge side, and lid latch side; and (g) a plurality of caddies removably attachable to the PALS strips;

(h) whereby all non-removable components of the case are composed exclusively of materials that are cleanable with bleach or hospital-grade wipes.

14. The carry bag of claim 13 wherein the mounting brackets are powder-coated or anodized aluminum.

15. The carry bag of claim 13 wherein the male component of the latch is adjustably attached to the latch webbing.

16. The carry bag of claim 13 wherein the hinge and latch webbings are coated with a polyurethane, thermoplastic polyurethane, or polyvinyl chloride.

17. The carry bag of claim 13 further comprising a removable divider in the lid generally parallel to the lid hinge side and lid latch side, the divider having PALS strips thereon, the PALS strips composed of nylon or polyvinyl chloride webbing.

18. The carry bag of claim 13 further comprising removable shoulder straps.

19. The carry bag of claim 13 further comprising a cylinder harness including a strap permanently attached to the case in the cylinder recess and at least one elastic band adapted to extend around the gas cylinder.

* * * * *